United States Patent [19]

Bovy et al.

[11] Patent Number: 5,378,727

[45] Date of Patent: Jan. 3, 1995

[54] SUBSTITUTED BICYCLIC HETEROCYCLIC COMPOUNDS USEFUL AS PLATELET AGGREGATION INHIBITORS

[75] Inventors: Philippe R. Bovy; Joseph G. Rico; Thomas E. Rogers, all of Ballwin; Foe S. Tjoeng, Manchester, all of Mo.; Jeffery A. Zablocki, Skokie, Ill.

[73] Assignee: G. D. Searle & Co., Chicago, Ill.

[21] Appl. No.: 94,666

[22] Filed: Jul. 19, 1993

Related U.S. Application Data

[60] Division of Ser. No. 953,661, Oct. 19, 1992, Pat. No. 5,254,573, which is a continuation-in-part of Ser. No. 888,686, May 22, 1992, abandoned, which is a continuation-in-part of Ser. No. 777,875, Oct. 15, 1991, abandoned.

[51] Int. Cl.$^6$ .................... C07D 319/14; A61K 31/36
[52] U.S. Cl. ..................... 514/465; 514/464; 549/436; 549/437; 549/438; 549/439; 549/441
[58] Field of Search ............... 549/436, 437, 439, 440, 549/441; 514/463, 464, 465; 548/438

[56] References Cited

U.S. PATENT DOCUMENTS

| | | | |
|---|---|---|---|
| 4,517,686 | 5/1985 | Ruoslahti et al. | 260/112.5 |
| 4,578,079 | 3/1986 | Ruoslahti et al. | 623/11 |
| 4,589,881 | 5/1986 | Pierschbacher et al. | 623/11 |
| 4,614,517 | 9/1986 | Ruoslahti et al. | 623/11 |
| 4,661,111 | 4/1987 | Ruoslahti et al. | 623/11 |
| 4,683,291 | 7/1987 | Zimmerman et al. | 530/324 |
| 4,857,508 | 8/1989 | Adams et al. | 514/18 |
| 4,879,313 | 11/1989 | Tjoeng et al. | 514/18 |
| 5,039,805 | 8/1991 | Alig et al. | 514/18 |
| 5,053,393 | 10/1991 | Tjoeng et al. | 514/18 |

FOREIGN PATENT DOCUMENTS

| | | | |
|---|---|---|---|
| 372486 | 10/1989 | European Pat. Off. | 514/18 |
| 445796 | 3/1990 | European Pat. Off. | 623/11 |

OTHER PUBLICATIONS

Koczewiak et al., *Biochem* 23, 1767–1774 (1984).
Plow et al., *Proc. Natl. Acad. Sci.* 82, 8057–8061 (1985).
Ruggeri et al., *Proc. Natl. Acad. Sci.* 83, 5708–5712 (1986).
Haverstick et al., *Blood* 66 (4), 946–952 (1985).
Ruoslahti and Pierschbacher, *Science* 238, 491–497 (1987).
R. T. Boere et al, *J. Organomet. Chem.*, 331, 161–67 (1987).
W. E. Parham, C. K. Bradsher, *Acct. Chem. Res.* 300 (1982).
M. Taddei and Ricci, *Synthesis* 633–635 (1986).
Allen, C. F. and Gates, J. W., *Org. Synth. Coll.* vol. 3, 140–141 (1955).
Ginsberg et al., *J. Biol. Chem.* 260 (7), 3931–3936 (1985).

*Primary Examiner*—C. Warren Ivy
*Assistant Examiner*—Zinna N. Davis
*Attorney, Agent, or Firm*—Cynthia S. Kovacevic; Roger A. Williams

[57] ABSTRACT

Novel substituted heterocyclic derivatives are provided which inhibit platelet aggregation. This invention also pertains to pharmaceutical compositions and methods of using such derivatives.

25 Claims, No Drawings

SUBSTITUTED BICYCLIC HETEROCYCLIC COMPOUNDS USEFUL AS PLATELET AGGREGATION INHIBITORS

This is a division of application Ser. No. 07/953,661, filed Oct. 6, 1992 now U.S. Pat. No. 5,254,573 which application is a continuation-in-part of U.S. patent application Ser. No. 07/888,686 filed May 2, 1992 which in turn is a continuation-in-part of U.S. patent application Ser. No. 07/777,875 filed Oct. 15, 1991, now abandoned.

BACKGROUND OF THE INVENTION

1. Field of the Invention

This invention pertains to substituted heterocyclic derivatives which inhibit platelet aggregation.

2. Related Art

Fibrinogen is a glycoprotein present as a normal component of blood plasma. It participates in platelet aggregation and fibrin formation in the blood clotting mechanism.

Platelets are cellular elements found in whole blood which also participate in blood coagulation. Fibrinogen binding to platelets is important to normal platelet function in the blood coagulation mechanism. When a blood vessel receives an injury, the platelets binding to fibrinogen will initiate aggregation and form a thrombus. Interaction of fibrinogen with platelets occurs through a membrane glycoprotein complex, known as gpIIb-/IIIa; this is an important feature of the platelet function. Inhibitors of this interaction are useful in modulating or preventing platelet thrombus formation.

It is also known that another large glycoprotein named fibronectin, which is a major extracellular matrix protein, interacts with fibrinogen and fibrin, and with other structural molecules such as actin, collagen and proteoglycans. Various relatively large polypeptide fragments in the cell-binding domain of fibronectin have been found to have cell-attachment activity. (See U.S. Pat. Nos. 4,517,686, 4,589,881, and 4,661,111). Certain relatively short peptide fragments from the same molecule were found to promote cell attachment to a substrate when immobilized on the substrate or to inhibit attachment when in a solubilized or suspended form. (See U.S. Pat. Nos. 4,578,079 and 4,614,517).

In U.S. Pat. No. 4,683,291, inhibition of platelet function is disclosed with synthetic peptides designed to be high affinity antagonists of fibrinogen binding to platelets. U.S. Pat. No. 4,857,508 discloses tetrapeptides having utility as inhibitors of platelet aggregation.

Other synthetic peptides and their use as inhibitors of fibrinogen binding to platelets are disclosed by Koczewiak et al., *Biochem.* 23, 1767–1774 (1984); Plow et al., *Proc. Natl. Acad. Sci.* 82, 8057–8061 (1985); Ruggeri et al., *Ibid.* 83, 5708–5712 (1986); Ginsberg et al., *J. Biol. Chem.* 260 (7), 3931–3936 (1985); Haverstick et al., *Blood* 66 (4), 946–952 (1985); and Ruoslahti and Pierschbacher, *Science* 238, 491–497 (1987). Still other such inhibitory peptides are disclosed in EP Pat. Applications 275,748 and 298,820.

U.S. Pat. No. 4,879,313 discloses compounds useful as inhibitors of platelet aggregation having the formula:

$$\begin{array}{c} HN \\ \phantom{HN}\diagdown \\ \phantom{HN}\phantom{\diagdown}HN-(CH_2)_x-CO-Asp-NH-CHZ-(CH_2)_y-Ar \\ H_2N \end{array}$$

wherein
x=6 to 10,
y=0 to 4,
Z=H, COOH, CONH2 or C1–6 alkyl,
Ar=phenyl, biphenyl or naphthyl, each substituted with 1 to 3 methoxy groups, or an unsubstituted phenyl, biphenyl, naphthyl, pyridinyl or thienyl group, and
Asp=aspartic acid residue.

European Patent Application 372,486 discloses N-acyl beta amino acid derivatives of the formula:

$$R^1-CONH-(CH_2)_{0-1}-\underset{R^2}{\underset{|}{\bigodot}}-(CH_2)_{0-1}-CONH-CHR^3-CH_2-CO_2H$$

and their salts. Said compounds are useful for inhibiting platelet aggregation in the treatment of thrombosis, stroke, myocardial infarction, inflammation and arteriosclerosis, and for inhibiting metastasis.

European Patent Application 381,033 discloses amidino or guanidinoaryl substituted alkanoic acid derivatives useful for the treatment of thrombosis, apoplexy, cardiac infarction, inflammation, arteriosclerosis and tumors.

European Patent Application 445,796 discloses Acetic Acid derivatives useful as a ligand for adhesive proteins on platelets. As such these compounds are useful to modulate and/or inhibit platelet aggregation.

SUMMARY OF THE INVENTION

In accordance with the present invention novel substituted heterocyclic derivatives are provided which modulate and/or inhibit platelet aggregation. These novel inhibitor compounds can be represented by the following chemical formula.

$$\begin{array}{cc} & Z'' \\ & | \\ HN & Z'-C-CO_2W \\ \diagdown & | \\ H_2N-\bigodot_{Z}^{R^1} & \\ & N-CO-A-CO-NH-C-(CH_2)_q-R^2 \\ & H \end{array} \quad (I)$$

or a pharmaceutically acceptable salt, prodrug or ester thereof, wherein R[1] is selected from the group consisting of hydrogen, lower alkyl radicals, lower alkenyl radicals, lower alkynyl radicals, alicyclic hydrocarbon radicals, aromatic hydrocarbon radicals, wherein all of said radicals are optionally substituted with hydroxyl, lower alkoxy, lower alkyl, halogen, nitro, carboxyl, sulfonyl, trifluoromethyl, amino, acyloxy, phenyl and naphthyl which are optionally substituted with halogen, nitro, lower alkoxy, and lower alkyl;

$R^2$ is selected from monocyclic, bicyclic or tricyclic heterocyclyl radicals in which 1 to about 3 heteroatoms are independently selected from oxygen, nitrogen and sulfur, which are optionally substituted with hydroxyl, lower alkoxy, lower alkyl, halogen, nitro, carboxyl, sulfonyl, trifluoromethyl, amino, acyloxy, phenyl and naphthyl which are optionally substituted with halogen, nitro, lower alkoxy, and lower alkyl;

A is selected from the group consisting of lower alkyl radicals, lower alkenyl radicals, lower alkynyl radicals, alicyclic radicals, wherein all of said radicals are optionally substituted with hydroxyl, lower alkoxy, lower alkyl, halogen, aromatic hydrocarbons which are optionally substituted with halogen, nitro, lower alkoxy and lower alkyl;

W is selected from the group consisting of hydrogen, lower alkyl radicals, lower alkenyl radicals, lower alkynyl radicals, alicyclic hydrocarbon radicals and aromatic hydrocarbon radicals, wherein all of said radicals are optionally substituted with hydroxyl, lower alkoxy, lower alkyl, halogen, nitro, amino, acyloxy, phenyl and naphthyl which may be optionally substituted with halogen, nitro, lower alkoxy, and lower alkyl;

Z, Z', Z" are independently selected from the group consisting of hydrogen, lower alkyl radicals, halogen, alkoxy, cyano, sulfonyl, carboxyl, and hydroxyl radicals; and q is an integer from 0 to about 6.

Preferably the above formula covers the compound and the pharmaceutically acceptable salts, and esters thereof.

$R^1$ is preferably selected from the group consisting of hydrogen, lower alkyl, aromatic hydrocarbon radicals; more preferably hydrogen, lower alkyl, benzyl, and phenyl; even more preferably hydrogen, lower alkyl and benzyl radicals; most preferably hydrogen.

$R^1$ is preferably optionally substituted with nitro, amino or lower alkoxy.

$R^2$ is preferably pyridinyl, pyrimidinyl, furanyl, thiophenyl or benzodioxolyl radicals which are optionally substituted with hydroxyl, lower alkoxy, lower alkyl, halogen, nitro, carboxyl, sulfonyl, trifluoromethyl and amino; more preferably pyridinyl and pyrimidinyl and benzodioxolyl; even more preferably pyridinyl.

$R^2$ is preferably optionally substituted with nitro, amino or lower alkoxy.

A is preferably lower alkyl, lower alkenyl radicals and lower alicyclic hydrocarbon radicals; more preferably lower alkyl or cyclopropylene.

W is preferably selected from pivaloyloxymethyl acyloxymethyl, hydrogen and lower alkyl radicals and more preferably is hydrogen and lower alkyl.

Z, Z', Z" are preferably hydrogen.

q is preferably 0 to about 4; more preferably 0 to about 2; most preferred 0.

It is another object of the invention to provide a novel pharmaceutical composition comprising compounds of the formula I useful in inhibiting or modulating platelet aggregation or the like. Particularly in inhibiting or modulating platelet aggregation by administering an amount between 0.5 mg/kg to 10 mg/kg, preferably 3 mg/kg to an animal in need thereof.

It is still another object of the invention to provide a method to therapeutically inhibit or modulate platelet aggregation or the like in a mammal in need of such treatment with a compound of the formula I in unit dosage form.

Many other objects and purposes of the invention will be clear from the following detailed description of the invention and examples.

DETAILED DESCRIPTION OF THE INVENTION

A preferred embodiment of the present invention is a compound of the formula I, pharmaceutically acceptable salt, prodrug or ester thereof;

wherein $R^1$ is selected from hydrogen, lower alkyl radicals of 1 to about 6 carbon atoms, lower alkenyl radicals of 2 to about 6 carbon atoms, lower alkynyl radicals of 2 to about 8 carbon atoms, alicyclic hydrocarbon radicals of 3 to about 6 carbon atoms, aromatic hydrocarbon radicals, wherein all of said radicals are optionally substituted with hydroxyl, lower alkoxy, lower alkyl, halogen, nitro, carboxyl, sulfonyl, and trifluoromethyl;

$R^2$ is selected from monocyclic or bicyclic heterocyclyl radicals in which 1 to about 3 heteroatoms are independently selected from oxygen, nitrogen and sulfur which are optionally substituted with hydroxyl, lower alkoxy, lower alkyl, halogen, nitro, carboxyl, sulfonyl, trifluoromethyl and amino;

A is selected from lower alkyl radicals of 1 to about 6 carbon atoms, lower alkenyl radicals of 2 to about 6 carbon atoms, lower alkynyl radicals of 2 to about 4 carbon atoms, and alicyclic hydrocarbon radicals of 3 to about 5 carbon atoms, wherein said radicals are optionally substituted with hydroxyl, lower alkoxy, and halogen;

W is selected from hydrogen, lower alkyl radicals of 1 to about 6 carbon atoms, lower alkenyl radicals of 2 to about 6 carbon atoms, alicyclic hydrocarbon radicals of 3 to about 6 carbon atoms, and aromatic hydrocarbon radicals of 6 to about 12 carbon atoms, wherein all of said radicals are optionally substituted with hydroxyl, lower alkoxy, lower alkyl, halogen, nitro, amino, and acyloxy;

Z, Z', Z" are independently selected from the group consisting of hydrogen, halogen, alkoxy, cyano, sulfonyl, carboxyl and lower alkyl radicals.

q is an integer from 0 to about 6.

$R^1$ is preferably hydrogen.

$R^2$ is preferably pyridinyl and pyrimidinyl and more preferably pyridinyl.

A is preferably lower alkyl of 1 to about 6 carbon atoms.

W is preferably selected from pivaloyloxymethyl acyloxymethyl, hydrogen and lower alkyl radicals and more preferably is hydrogen and lower alkyl; most preferably hydrogen and ethyl.

Z, Z', Z" are preferably hydrogen.

Another preferred embodiment of the present invention is a compound of the formula I, pharmaceutically acceptable salt, prodrug or ester thereof;

wherein $R^1$ is selected from hydrogen, lower alkyl radicals, phenyl radicals, benzyl radicals, substituted phenyl radicals wherein each substituent are selected from the group consisting of halogen, lower alkyl, lower alkoxy and carboxyl radicals;

$R^2$ is selected from monocyclic or bicyclic heterocyclyl radicals in which 1 to about 3 heteroatoms are nitrogen which are optionally substituted with hydroxyl, lower alkoxy, lower alkyl, halogen, nitro, carboxyl, sulfonyl, trifluoromethyl and amino;

A is selected from lower alkyl radicals and lower alkenyl radicals and lower alicyclic hydrocarbon radicals;

W is selected from the group consisting of hydrogen and lower alkyl radicals;

Z, Z', Z'' are independently selected from the group consisting of halogen and hydrogen, and alkoxy, and lower alkyl radicals; and q is an integer from 0 to about 6.

$R^1$ is preferably hydrogen, lower alkyl radicals, phenyl radicals; more preferably hydrogen.

$R^2$ is preferably pyridinyl and pyrimidinyl; more preferably pyridinyl,

A is preferably lower alkyl.

W is preferably selected from hydrogen and lower alkyl radicals; more preferably hydrogen and ethyl.

Z, Z', Z'' are preferably hydrogen.

q is preferably an integer 0 to about 4; more preferably 0 to about 2 and most preferably 0.

In the Formula I, $R^1$ can additionally form a cyclic structure with the adjacent phenyl ring.

It is contemplated that the following compounds should be exemplifying examples:

methyl-D,L-$\beta$-[[4-[[4-(aminoiminomethyl)phenyl]amino]-1,4-dioxobutyl]amino]-3-pyridinyl propanoate;

isopropyl-D,L-$\beta$-[[4-[[4-(aminoiminomethyl)phenyl]amino]-1,4-dioxobutyl]amino]-3-pyridinyl propanoate;

cyclopropyl-D,L-$\beta$-[[4[[4-(aminoiminomethyl)phenyl]amino]-1,4-dioxobutyl]amino]-3-pyridinyl propanoate;

hexyl-D,L-$\beta$-[[4-[[4-aminoiminomethyl)phenyl]amino]-1,4-dioxobutyl]amino]-4-pyridinyl propanoate;

D,L-$\beta$-[[4-[[4-(aminoiminomethyl)phenyl]N-methylamino]-1,4-dioxobutyl]amino]-3-pyridinyl propionic acid;

D,L-$\beta$-[[4-[[4-(aminoiminomethyl)phenyl]N-phenylamino]-1,4-dioxobutyl]amino]-3-pyridinyl propionic acid;

D,L-$\beta$-[[4-[[4-(aminoiminomethyl)phenyl]amino]-1,4-dioxobutynyl]amino]-2-pyridinyl propionic acid;

D,L-$\beta$-[[4-[[3-methyl-4-(aminoiminomethyl)phenyl]amino]-1,4-dioxobutyl]amino]-3-pyridinyl propionic acid;

D,L-$\beta$-[[4-[[2-fluoro-4-(aminoiminomethyl)phenyl]amino]-1,4-dioxobutyl]amino]-3-pyridinyl propionic acid;

D,L-$\beta$-[[4-[[2,6-difluoro-4-(aminoiminomethyl) phenyl]amino]-1,4-dioxobutyl]amino]-2-pyridinyl propionic acid;

D,L-$\beta$-[[4-[[4-(aminoiminomethyl)naphthyl]amino]-1,4-dioxobutyl]amino]-3-pyridinyl propionic acid;

D,L-$\beta$-[[4-[[4-(aminoiminomethyl)phenyl]amino]-1,4-dioxo-2,2,3,3-tetrafluorobutyl]amino]-4-pyridinyl propionic acid;

ethyl-D,L-$\beta$-[[4-[[4-(aminoiminomethyl)phenyl]N-methylamino]-1,4-dioxobutyl]amino]-3-pyridinyl propanoate;

ethyl-D,L-$\beta$-[[4-[[4-(aminoiminomethyl)phenyl]amino]-1,4-dioxobutynyl]amino]-3-pyridinyl propanoate;

ethyl-D,L-$\beta$-[[4-[[4-(aminoiminomethyl)phenyl]N-phenylamino]-1,4-dioxobutyl]amino]-2-pyridinyl propanoate;

ethyl-D,L-$\beta$[[4-[[3-methyl-4-(aminoiminomethyl) phenyl]amino]-1,4-dioxobutyl]amino]-3-pyridinyl propanoate;

ethyl-D,L-$\beta$-[[4-[[2-fluoro-4-(aminoiminomethyl) phenyl]amino]-1,4-dioxobutyl]amino]-3-pyridinyl propanoate;

ethyl-D,L-$\beta$-[[4-[[2,6-difluoro-4-(aminoiminomethyl) phenyl]amino]-1,4-dioxobutyl]amino]-2-pyridinyl propanoate;

ethyl-D,L-$\beta$-[[4-[[4-(aminoiminomethyl)naphthyl]amino]-1,4-dioxobutyl]amino]-3-pyridinyl propanoate;

ethyl-D,L-$\beta$-[[4-[4-aminoiminomethyl)phenyl]amino]-1,4-dioxo-2,2,3,3-tetrafluorobutyl]amino]-3-pyridinyl propanoate;

$\beta$-[[[2-[[[4-(aminoiminomethyl)phenyl]amino]carbonyl]cyclopropyl]carbonyl]amino]-4-pyridinyl propionic acid;

$\beta$-[[[2-[[[4-(aminoiminomethyl)phenyl]amino]carbonyl]cyclobutyl]carbonyl]amino]-3-pyridinyl propionic acid;

$\beta$-[[[2-[[[4-(aminoiminomethyl)phenyl]amino] carbonyl]cyclopentyl]carbonyl]amino]-3-pyridinyl propionic acid;

$\beta$-[[[2-[[[4-(aminoiminomethyl)phenyl]amino]carbonyl]cyclohexyl]carbonyl]amino]-3-pyridinyl propionic acid;

ethyl-$\beta$-[[[2-[[[4-(aminoiminomethyl)phenyl]amino]carbonyl]cyclopropyl]carbonyl]amino]-4-pyridinyl propanoate;

ethyl-$\beta$-[[[2-[[[4-(aminoiminomethyl)phenyl]amino]carbonyl]cyclobutyl]carbonyl]amino]-3-pyridinyl propanoate;

ethyl-$\beta$-[[[2[[[4-(aminoiminomethyl)phenyl]amino]carbonyl]cyclopentyl]carbonyl]amino]-3-pyridinyl propanoate;

ethyl-$\beta$-[[[2-[[[4-(aminoiminomethyl)phenyl]amino]carbonyl]cyclohexyl]carbonyl]amino]-2-pyridinyl propanoate;

methyl-D,L-$\beta$-[[4-[[4-(aminoiminomethyl)phenyl]amino]-1,4-dioxobutyl]amino]-2-(1,3)-pyrimidinyl-propanoate;

isopropyl-D,L-$\beta$-[[4-[[4-(aminoiminomethyl)phenyl]amino]-1,4-dioxobutyl]amino]-2-(1,3)pyrimidinyl propanoate;

cyclopropyl-D,L-$\beta$-[[4-[[4-(aminoiminomethyl) phenyl]amino]-1,4-dioxobutyl]amino]-2-(1,3)-pyrimidinyl-propanoate;

hexyl-D,L-$\beta$-[[4-[[4-(aminoiminomethyl)phenyl]amino]-1,4-dioxobutyl]amino]-2-(1,3)-pyrimidinyl-propanoate;

D,L-$\beta$-[[4-[[4-(aminoiminomethyl)phenyl]-N-methylamino]-1,4-dioxobutyl]amino]-2-(1,3)pyrimidinylpropionic acid;

D,L-$\beta$-[[4-[[4-(aminoiminomethyl)phenyl]-N-phenylamino]-1,4-dioxobutyl]amino]-2-(1,3)pyrimidinylpropionic acid;

D,L-$\beta$-[[4-[[4-(aminoiminomethyl)phenyl]amino]-1,4-dioxobutynyl]amino]-2-pyridazinylpropionic acid;

D,L-$\beta$-[[4-[[3-methyl-4-(aminoiminomethyl) phenyl]amino]-1,4-dioxobutyl]amino]-2-pyridazinylpropionic acid;

D,L-$\beta$-[[4-[[2-fluoro-4-(aminoiminomethyl)phenyl]amino]-1,4-dioxobutyl]amino]-2-pyridazinylpropionic acid;

D,L-β-[[4-[[2,6-difluoro-4-(aminoiminomethyl) phenyl]amino]-1,4-dioxobutyl]amino]-2-thiazolylpropionic acid;

D,L-β-[[4-[[4-(aminoiminomethyl)naphthyl]amino]-1,4-dioxobutyl]amino]-2-thiazolylpropionic acid;

D,L-β-[[4-[[4-(aminoiminomethyl)phenyl]amino]-1,4-dioxobutyl]amino]-2-thiazolylpropionic acid;

ethyl-D,L-β-[[4-[[4-(aminoiminomethyl)phenyl]-N-methylamino]-1,4-dioxobutyl]amino]-2-thiazolylpropanoate;

ethyl-D,L-β-[[4-[[4-(aminoiminomethyl)phenyl]amino]-1,4-dioxobutynyl]amino]-2-thiazolylpropanoate;

ethyl-D,L-β-[[4-[[4-(aminoiminomethyl)phenyl]-N-phenylamino]-1,4-dioxobutyl]amino]-2thiazolylpropanoate;

ethyl-D,L-β-[[4-[[3-methyl-4-(aminoiminomethyl) phenyl]amino]-1,4-dioxobutyl]amino]-2-thiazolylpropanoate;

ethyl-D,L-β-[[4-[[2-fluoro-4-(aminoiminomethyl) phenyl]amino]-1,4-dioxobutyl]amino]-2-thiazolylpropanoate;

ethyl-D,L-β-[[4-[[2,6-difluoro-4-(aminoiminomethyl)phenyl]amino]-1,4-dioxobutyl]amino]-2-(1,3)-pyrimidinylpropanoate;

ethyl-D,L-β-[[4-[[4-(aminoiminomethyl)naphthyl]amino]-1,4-dioxobutyl]amino]-2-(1,3)-pyrimidinylpropanoate;

ethyl-D,L-β-[[4-[[4-(aminoiminomethyl)phenyl]amino]-1,4-dioxo-2,2,3,3-tetrafluorobutyl]amino]-2-(1,3)-pyrimidinylpropanoate;

β-[[[2-[[[4-(aminoiminomethyl)phenyl]amino]carbonyl]cyclopropyl]carbonyl]amino]-2-(1,3)-pyrimidinylpropionic acid;

β-[[[2-[[[4-(aminoiminomethyl)phenyl]amino]carbonyl]cyclobutyl]carbonyl]amino]-2-pyridazinylpropionic acid;

β-[[[2-[[[4-(aminoiminomethyl)phenyl]amino]carbonyl]cyclopentyl]carbonyl]amino]-2-oxazolylpropionic acid;

β-[[[2-[[[4-(aminoiminomethyl)phenyl]amino]carbonyl]cyclohexyl]carbonyl]amino]-2-oxazolylpropionic acid;

ethyl-β-[[[2-[[[4-(aminoiminomethyl)phenyl]amino]carbonyl]cyclopropyl]carbonyl]amino]-2-thiazolylpropanoate;

ethyl-β-[[[2-[[[4-(aminoiminomethyl)phenyl]amino]carbonyl]cyclobutyl]carbonyl]amino]-2-pyrrolylpropanoate;

methyl-D,L-β-[[4-[[4-(aminoiminomethyl)phenyl]amino]-1,4-dioxobutyl]amino]-3-imidazolylpropanoate;

isopropyl-D,L-β-[[4-[[4-(aminoiminomethyl)phenyl]amino]-1,4-dioxobutyl]amino]-3-imidazolylpropanoate;

cyclopropyl-D,L-β-[[4-[[4-(aminoiminomethyl)phenyl]amino]-1,4-dioxobutyl]amino]-3-imidazolylpropanoate;

hexyl-D,L-β-[[4-[[4-(aminoiminomethyl) phenyl]amino]-1,4-dioxobutyl]amino]-3-imidazolylpropanoate;

D,L-β-[[4-[[4-(aminoiminomethyl)phenyl]-N-methylamino]-1,4-dioxobutyl]amino]-3-imidazolylpropionic acid;

D,L-β-[[4-[[4-(aminoiminomethyl)phenyl]-N-phenylamino]-1,4-dioxobutyl]amino]-3-imidazolylpropionic acid;

D,L-β-[[4-[[4-(aminoiminomethyl)phenyl]amino]-1,4-dioxobutynyl]amino]-2-imidazolylpropionic acid;

D,L-β-[[4-[[3-methyl-4-(aminoiminomethyl)phenyl]amino]-1,4-dioxobutyl]amino]-3-pyrazolylpropionic acid;

D,L-β-[[4-[[2-fluoro-4-(aminoiminomethyl)phenyl]amino]-1,4-dioxobutyl]amino]-2-imidazolylpropionic acid;

D,L-β-[[4-[[2,6-difluoro-4-(aminoiminomethyl) phenyl]amino]-1,4-dioxobutyl]amino]-3-pyrazolylpropionic acid;

D,L-β-[[4-[[4-(aminoiminomethyl)naphthyl]amino]-1,4-dioxobutyl]amino]-2-imidazolylpropionic acid;

D,L-β-[[4-[[4-(aminoiminomethyl)phenyl]amino]-1,4-dioxo-2,2,3,3-tetrafluorobutyl]amino]-3-pyrazolylpropionic acid;

ethyl-D,L-β-[[4-[[4-(aminoiminomethyl) phenyl]amino]-1,4-dioxobutyl]amino]-2-imidazolylpropanoate;

ethyl-D,L-β-[[4-[[4-(aminoiminomethyl) phenyl]amino]-1,4-dioxobutynyl]amino]-3-pyrazolylpropanoate;

ethyl-D,L-β-[[4-[[4-(aminoiminomethyl)phenyl]-N-phenylamino]-1,4-dioxobutyl]amino]-2-imidazolylpropanoate;

ethyl-D,L-β-[[4-[[3-methyl-4-(aminoiminomethyl) phenyl]amino]-1,4-dioxobutyl]amino]-3-triazolylpropanoate;

ethyl-D,L-β-[[4-[[2-fluoro-4-(aminoiminomethyl) phenyl]amino]-1,4-dioxobutyl]amino]-2-imidazolylpropanoate;

ethyl-D,L-β-[[4-[[2,6-difluoro-4-(aminoiminomethyl)phenyl]amino]-1,4-dioxobutyl]amino]-3-triazolylpropanoate;

ethyl-D,L-β-[[4-[[4-(aminoiminomethyl) naphthyl]amino]-1,4-dioxobutyl]amino]-2-imidazolylpropanoate;

ethyl-D,L-β-[[4-[[4-(aminoiminomethyl)phenyl]amino]-1,4-dioxo-2,2,3,3-tetrafluorobutyl]amino]-3-triazolylpropanoate;

β-[[[2-[[[4-(aminoiminomethyl)phenyl]amino]carbonyl]cyclopropyl]carbonyl]amino]-2-imidazolylpropionic acid;

β-[[[2-[[[4-(aminoiminomethyl)phenyl]amino]carbonyl]cyclobutyl]carbonyl]amino]-3-pyrazolylpropionic acid;

β-[[[2-[[[4-(aminoiminomethyl)phenyl]amino]carbonyl]cyclopentyl]carbonyl]amino]-2-imidazolylpropionic acid;

β-[[[2-[[[4-(aminoiminomethyl)phenyl]amino]carbonyl]cyclohexyl]carbonyl]amino]-3-imidazolylpropionic acid;

ethyl-β-[[[2-[[[4-(aminoiminomethyl)phenyl]amino]carbonyl]cyclopropyl]carbonyl]amino]-3-pyrrolylpropanoate;

ethyl-β-[[[2-[[[4-(aminoiminomethyl)phenyl]amino]carbonyl]cyclobutyl]carbonyl]amino]- 3-thienylpropanoate;

ethyl-β-[[[2-[[[4-(aminoiminomethyl)phenyl]amino]carbonyl]cyclopentyl]carbonyl]amino]-3-indolylpropanoate;

ethyl-D,L-β-[[4-[[4-(aminoiminomethyl)phenyl]N-methylamino]-1,4-dioxobutyl]amino]-2-furanylpropanoate;

ethyl-D,L-β-[[4-[[4-(aminoiminomethyl)phenyl]amino]-1,4-dioxobutynyl]amino]-2-furanylpropanoate;

ethyl-D,L-β-[[4-[[4-(aminoiminomethyl) phenyl]amino]-1,4-dioxobutyl]amino]-2-oxazolylpropanoate;

ethyl-D,L-β-[[4-[[3methyl-4-(aminoiminomethyl) phenyl]amino]-1,4-dioxobutyl]amino]-3-triazolyl-propanoate;

As utilized herein, the term "lower alkyl", alone or in combination, means an acyclic alkyl radical containing from 1 to about 10, preferably from 1 to about 8 carbon atoms and more preferably 1 to about 6 carbon atoms. Examples of such radicals include methyl, ethyl, n-propyl, isopropyl, n-butyl, isobutyl, sec-butyl, tert-butyl, pentyl, iso-amyl, hexyl, octyl and the like.

The term "lower alkenyl" refers to an unsaturated acyclic hydrocarbon radical in so much as it contains at least one double bond. Such radicals containing from about 2 to about 10 carbon atoms, preferably from about 2 to about 8 carbon atoms and more preferably 2 to about 6 carbon atoms. Examples of suitable alkenyl radicals include propylenyl, buten-1-yl, isobutenyl, penten-1-yl, 2-2-methylbuten-1-yl, 3-methylbuten-1-yl, hexen-1-yl, hepten-1-yl, and octen-1-yl and the like.

The term "lower alkynyl" refers to an unsaturated acyclic hydrocarbon radicals in so much as it contains one or more triple bonds, such radicals containing about 2 to about 10 carbon atoms, preferably having from about 2 to about 8 carbon atoms and more preferably having 2 to about 6 carbon atoms. Examples of suitable alkynyl radicals include ethynyl, propynyl, butyn-1-yl, butyn-2-yl, pentyn-1-yl, pentyn-2-yl, 3-methylbutyn-1-yl, hexyn-1-yl, hexyn-2-yl, hexyn-3-yl, 3,3-dimethyl-butyn-1-yl radicals and the like.

The term "alicyclic hydrocarbon" means a aliphatic radical in a ring with 3 to about 10 carbon atoms, and preferably from 3 to about 6 carbon atoms. Examples of suitable alicyclic radicals include cyclopropyl, cyclopropylenyl, cyclobutyl, cyclopentyl, cyclohexyl, 2-cyclohexen-1-ylenyl, cyclohexenyl and the like.

The term "heterocyclyl radical" means a heterocyclyl hydrocarbon radical preferably an aromatic heterocyclyl hydrocarbon radical with 4 to about 10 carbon atoms, preferably about 5 to about 6; wherein 1 to about 3 carbon atoms are replaced by nitrogen, oxygen or sulfur. The "heterocyclyl radical" may be fused to a aromatic hydrocarbon radical. Suitable examples include pyrrolyl, pyridinyl, pyrazolyl, pyrrolyl, triazolyl, pyrimidinyl, pyridazinyl, oxazolyl, thiazolyl, imidazolyl, indolyl, thiophenyl, furanyl, tetrazolyl, 2-pyrrolinyl, 3-pyrrolinyl, pyrrolidinyl, 1,3-dioxolanyl, 2-imidazolinyl, imidazolidinyl, 2pyrazolinyl, pyrazolidinyl, isoxazolyn, isothiazolyn, 1,2,3-oxadiazolyn, 1,2,3-triazolyn, 1,3,4-thiadiazolyn, 2H-pyranyl, 4H-pyranyl, piperidinyl, 1,4-dioxanyl, morpholinyl 1,4-dithianyl, thiomorpholinyl, pyrazinyl, piperazinyl, 1,3,5-triazinyl, 1,3,5-trithianyl, benzo(b)thiophenyl, benzimidazolyn, quinolinyl, and the like.

The term "aromatic hydrocarbon radical" means 4 to about 16 carbon atoms, preferably 6 to about 12 carbon atoms, more preferably 6 to about 10 carbon atoms. Examples of suitable aromatic hydrocarbon radicals include phenyl, naphthyl, and the like.

The term "acyloxy" means 1 to about 4 carbon atoms. Suitable examples include alkanoyloxy, benzoyloxy and the like.

The term "lower alkoxy", alone or in combination, means an alkyl ether radical wherein the term alkyl is as defined above and most preferably containing 1 to about 4 carbon atoms. Examples of suitable alkyl ether radicals include methoxy, ethoxy, n-propoxy, isopropoxy, n-butoxy, iso-butoxy, sec-butoxy, tert-butoxy and the like.

The term halogen means fluorine, chlorine, bromine or iodine.

The term "pharmaceutically acceptable salt" refers to a salt prepared by contacting a compound of formula (I), (II), or (III) with an acid whose anion is generally considered suitable for human consumption. Examples of pharmacologically acceptable salts include the hydrochloride, hydrobromide, hydroiodide, sulfate, phosphate, acetate, propionate, lactate, maleate, oxalate, malate, succinate, tartrate and citrate salts. All of these salts may be prepared by conventional means by reacting, for example, the appropriate acid with the corresponding compound of formula I.

The term "prodrug" refers to a compound that is made more active in vivo.

Suitable pharmaceutically-acceptable base addition salts of compounds of Formula I include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine.

Total daily dose administered to a host in single or divided doses may be in amounts, for example, from 0.001 to 100 mg/kg body weight daily and more usually 0.01 to 10 mg. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood that the specific dose level for any particular patient will depend upon a variety of factors including the activity of the specific compound employed, the age, body weight, general health, sex, diets, time of administration, route of administration, rate of excretion, drug combination, and the severity of the particular disease undergoing therapy.

The compounds of the present invention may be administered orally, parenterally, by inhalation spray, rectally, or topically in dosage unit formulations containing conventional nontoxic pharmaceutically acceptable carriers, adjuvants, and vehicles as desired.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectable.

Suppositories for rectal administration of the drug can be prepared by mixing the drug with a suitable nonirritating excipient such as cocoa butter and polyethylene glycols which are solid at ordinary temperature but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

While the compounds of the invention can be administered as the sole active pharmaceutical agent, they can also be used in combination with one or more active pharmaceutical agents. When administered as a combination, the therapeutic agents can be formulated as separate compositions which are given at the same time or different times, or the therapeutic agents can be given as a single composition.

In the structures and formulas herein, the bond drawn across a bond of an aromatic ring can be to any available atom on the aromatic ring.

The compounds of formula I can exist in various isomeric forms and all such isomeric forms are meant to be included. Tautomeric forms are also included in the invention. Pharmaceutically acceptable salts of such isomers and tautomers are meant to be included as well.

It is also contemplated that Beta amino acids ($H_2N$—CHR—$CH_2$—$CO_2H$) used in this invention may be replaced by Homo Beta amino acids ($H_2N$—$CH_2$—CHR—$CO_2H$).

The compounds listed above may be prepared by standard synthetic methods combined with methods analogous to solution phase peptide synthesis [see: The Peptides: Analysis, Synthesis, Biology (E. Gross and J. Meienhofer, eds.), (Vol. 1–5, Academic Press, New York)], the disclosure of which is hereby incorporated by reference.

Three general synthetic sequences are outlined in Schemes 1–3.

In Scheme I. The aminobenzamidine 1 (i.e., Z is hydrogen) is coupled to an alkanoic, alkenoic (both substituted or not) or alkynoic diacid. An activated form of the diacid is preferentially used. These activated forms include anhydrides, internal anhydride, acid chloride or one of the various activated forms as described in *Principles of Peptide Synthesis*, Bodansky, 1984, Springer-Verlag, the disclosure of which is hereby incorporated by reference. A highly preferred procedure involves condensation of an anhydride (e.g., succinic anhydride 2) with a salt of substituted aromatic 1. The reaction is best conducted in a polar solvent such as methylene chloride, acetonitrile, dioxane, dimethylformamide, dimethylsulfoxide or a mixture of such solvents in the presence of an acid binding agent such as sodium, potassium or cesium carbonate, triethylamine, pyridine, sodium hydride, dimethylaminopyridine, diazabicycloundecene, or a mixture of such agents, at temperatures ranging between 0° C. and 120° C. The final compounds are obtained by coupling of the amidine derivative 3 with a properly protected β-aminoacid. The amide bonds are formed using standard coupling reagents, e.g., dicyclohexylcarbodiimide (DCC), carbonyldiimidazole (CDI), disuccinimidyl carbonate (DSC), benzotriazole-1-yl-oxy-tris-(dimethylamino)-phosphonium hexafluorophosphate (BOP) or isobutyl chloroformate (mixed anhydride method). When the β-amino acid used in the coupling was protected as an ester of the carboxylic acid function (4, W=alkyl, aryl, . . . ), the free acids 5 are obtained by a suitable deprotection method as described by T. H. Greene in "*Protective Group in Organic Synthesis*", Wiley-Interscience, 1980, the disclosure of which is hereby incorporated by reference.

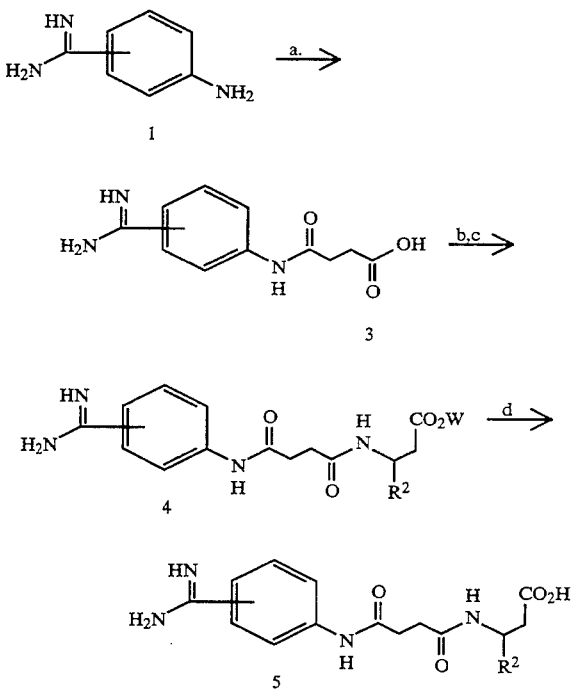

SCHEME I a. Succinic anhydride (2), pyridine, DMAP.
b. i-ButOCOCl, NMM.
c. β-Alanine derivative
d. NaOH or LiOH.

Wherein W and $R^2$ have the values described in formula I

Alternatively, an aminobenzonitrile 6 can be used for condensation with the desired diacid or diacid derivative. In this case, the nitrile can be converted to the amidine initially or at a later stage. When the aminobenzonitrile is used in the condensation reaction (Scheme II), the cyano group of the resulting intermediate 7 is converted to the amidine 8 via the thioimidate in nearly quantitative yield. The thioimidate is formed by first treating the cyano compound with hydrogen sulfide ($H_2S$) followed by alkylation with methyl iodide. Next, treatment of the thioimidate with ammonium acetate affords the amidine as the salt (HI). Alternatively, the nitrile 7 can be converted to the amidine 8 by the use of lithium bis(trimethylsilyl)amide in an inert solvent such as diethyl ether (R. T. Boere et al, *J. Organomet. Chem.*, 331, 161–67, 1987), the disclosure of which is hereby incorporated by reference. The desired compounds are obtained by coupling of the amidine derivative 8 with a properly functionalized β-aminoacid. The amide bonds are formed using standard coupling reagents as described above for Scheme I.

SCHEME II

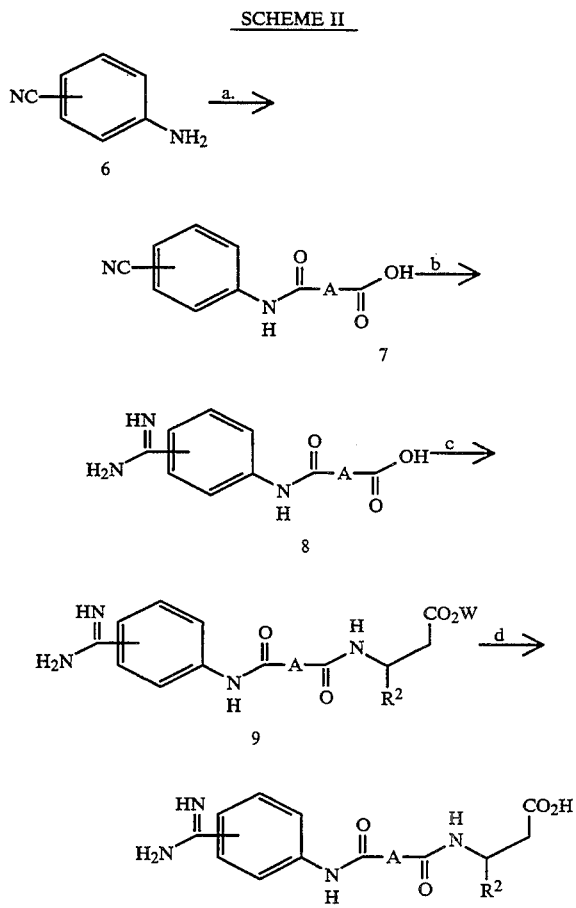

a. Activated diacid.
b. H2S, pyridine; MeI, acetone; NH Hexamethyl disilazane in diethyl ether.
c. Anhydride
d. Base or acid.

A, W and $R^2$ have the values described in the general fromula

Scheme III illustrates the obtention of derivatives using the amino nitriles as reagents. The cyano group is kept intact as a precursor for the amidine function throughout two amide bond forming steps. The first intermediate 10 is directly engaged in a reaction with the desired β-amino acid. The intermediate 10 is then converted to the benzamidine. A method of choice to produce the amidine function is via the thioimidate procedure as described in Scheme II. It is desirable, in Scheme III, to prepare the intermediate 11 as an ester. The most desirable ester is the t-butyl ester which can be deprotected to the acid by contact with a strong acidic medium as HBr/AcOH or trifluoroacetic acid/-dichloromethane.

SCHEME III

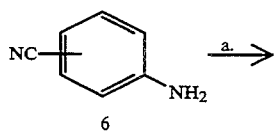

-continued
SCHEME III

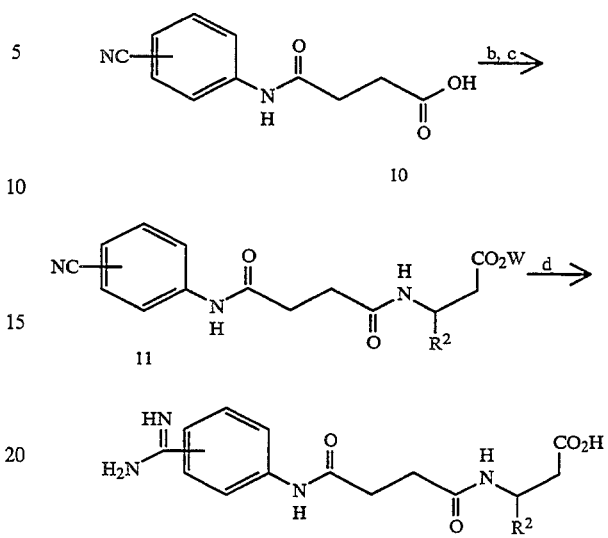

a. Succinic anhydride, pyridine, DMAP.
b. Anhydride mixte, NMM.
c. b-Alanine derivatives
d. H2S, pyridine MeI, acetone NH4OAc or Hexamethyl disilazane in diethyl ether.

The Z substituents, (where Z is hydrogen or halogen, or an alkyl radical or alkoxy radical) can be introduced at the aminobenzonitrile stage. The phenyl group can be halogenated using bromine, iodine, or chlorine. The alkyl group can be introduced by low temperature lithium halogen exchange followed by quenching with the appropriate aldehyde [see: W. E. Parham, C. K. Bradsher *Acct. Chem. Res.* 300 (1982)], the disclosure of which is hereby incorporated by reference. The resultant alcohol can be converted to Z is alkyl hydrogenolysis [Reductions in Organic Chemistry (M. Hudicky, ed.), John Wiley & Sons, New York, 1984]., the disclosure of which is hereby incorporated by reference. Where Z is hydroxy or alkoxy, such substituents can be introduced by low temperature lithium halogen exchange followed by quenching with electrophilic bis(-trimethylsilyl) peroxide [(TMSO)2] M. Taddei and A. Ricci *Synthesis* 633-635 (1986)], the disclosure of which is hereby incorporated by reference, which affords the silyl ether. The silyl ether can be converted to the hydroxy derivative by treatment with hydrochloric acid [M. Taddei and A. Ricci ibid]. The hydroxy in the presence of a weak base (K2C03) and an appropriate alkyl halide [R8-Hal, Allen C. F. and Gates J. W., Org. Synth. Coll. Vol 2 3 140 (1955), the disclosure of which is hereby incorporated by reference.] which will form the ester as well. The ester can be selectively cleaved in the presence of the ether with one equivalent of sodium hydroxide.

For derivatives wherein $R^1$ is different from hydrogen, such derivatives can be obtained by using an appropriately substituted aminobenzamidine. For example, the 4-methylaminobenzamidine can be reacted with succinic anhydride in a manner similar to the substituted heterocyclic.

Purification of final compounds is by reverse phase high pressure liquid chromatography [*High Performance Liquid Chromatography Protein and Peptide Chemistry*, F. Lottspeich, A. Henscher, K. P. Hupe, eds.) Walter DeGruyter, New York, 1981, the disclosure of which is hereby incorporated by reference.) or crystallization.

Contemplated equivalents of the general formulas set forth above for the platelet aggregation inhibitors and derivatives as well as the intermediates are compounds otherwise corresponding thereto and having the same general properties wherein one or more of the various R groups are simple variations of the substituents as defined therein, e.g., wherein R is a higher alkyl group than that indicated. In addition, where a substituent is designated as, or can be, a hydrogen, the exact chemical nature of a substituent which is other than hydrogen at that position, e.g., a hydrocarbyl radical or a halogen, hydroxy, amino and the like functional group, is not critical so long as it does not adversely affect the overall activity and/or synthesis procedure.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

Without further elaboration, it is believed that one skilled in the art can, using the preceding description, utilize the present invention to its fullest extent. Therefore the following preferred specific embodiments are to be construed as merely illustrative and not limitative of the remainder of the disclosure in any way whatsoever.

The following examples are provided to illustrate the present invention and are not intended to limit the scope thereof. Those skilled in the art will readily understand that known variations of the conditions and processes of the following preparative procedures can be used to prepare these compounds. All temperatures expressed are in degrees centigrade. Within the foregoing synthetic description and examples which follow, abbreviations have the following meanings:

CHCl$_3$=chloroform
DMF=dimethylformamide
DMSO=dimethylsulfoxide
g=gram
MeOH=methanol
min=minute
h=hour
mol=mole
mmol=millimole
MW=molecular weight
TLC=thin layer chromatography
NMM=N-methylmorpholine
RPHPLC=Reverse Phase High Pressure Liquid Chromatography

EXAMPLE 1

Ethyl-$\beta$-[[4-[[4-(aminoiminomethyl)phenyl]amino]-1,4-dioxobutyl]amino]-3-pyridinepropanoate

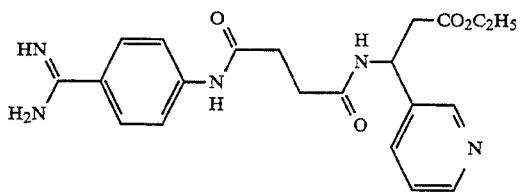

Step 1 Preparation of 4-[[4-(aminoiminomethyl)phenyl]amino]-4-oxobutanoic acid.

Aminobenzamidine di-HCl (25 g, 120 mmol), which is commercially available particularly from Aldrich, was added to dry DMF (100 ml). To this solution dry pyridine (100 ml) and succinic anhydride (12 g, 120 mmol) followed by dimethylaminopyridine (DMAP, 1.5 g, 12.2 mmol) were added. The product precipitated after heating for ½ h at 100° C. The product was filtered, washed with water, acetonitrile, and ether. The white solid was suspended in dioxane, 4N HCl in dioxane (100 ml) was added and the suspension was stirred for 1 h, filtered and dried in a desiccator to give 28 g, 88% of 4-[[4-(aminoiminomethyl)phenyl]amino]-4-oxobutanoic acid as a white yellow solid which decomposes between 270 and 290° C.

Step 2 Preparation of Ethyl-$\beta$-[[4-[[4-(aminoiminomethyl)phenyl]amino]-1,4-dioxobutyl]amino]-3-pyridinepropanoate An aliquot of 4-[[4-(aminoiminomethyl)phenyl]amino]-4-oxobutanoic acid hydrochloride prepared in Example 1, Step 1 (2.35 g) was added to dry DMF (100 ml), followed by N-methylmorpholine (1.1 mL) and isobutyl chloroformate (1.30 mL) at 0° C. under nitrogen atmosphere. The mixture was stirred for 5 min and 3.56 g of $\beta$-amino-3-pyridinepropionic acid ethyl ester dihydrochloride (75% pure) was added followed by 2.1 mL of N-methylmorpholine. After 1 h, the solvent was removed under reduced pressure and the product was purified by reverse phase chromatography (water/acetonitrile) to give 4.4 g of white solid: $^1$H NMR (d$_6$-DMSO) $\delta$1.12 (t, 3H,J=7 Hz), 2.45 (m, 2H), 2.6 (m, 2H), 2.85 (m, 2H), 4.05 (q, 2H,J=7 Hz), 5.28 (m, 1H), 7.55 (m, 1H), 7.8 (s, 4H), 8.0 (m, 1H), 8.6 (m, 3H), 8.85 (bs, 2H), 9.18 (bs, 2H), 10.4 (s, 1H); MS(ES) m/e 412.1 (MH+), 277,235,218.

Elemental Analysis Required for $C_{21}H_{25}N_5O_4.2F_3$-$C_2O_2H.H_2O$: C 45.67 H 4.45 N 10.65 Found: C 45.83 H 4.31 N 10.63

EXAMPLE 2

D,L-$\beta$2
-[[4-[[4-(aminoiminomethyl)phenyl]amino]-1,4-dioxobutyl]amino]-3 -pyridinepropanoic acid

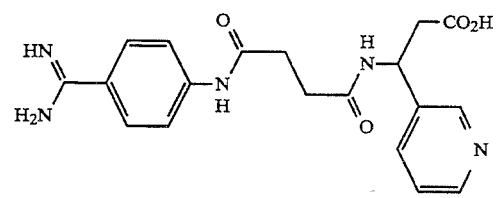

A portion of [[4-[[4-(aminoiminomethyl)phenyl]amino]-1,4-dioxobutyl]amino]-3-pyridinepropanoate (550 mg of the trifluoroacetate salt) prepared as in Example 1 was dissolved in 50 mL water and 300 uL of 50% sodium hydroxide. The reaction mixture was allowed to stir at 25° C. for 2 h, concentrated in vacuo, and was purified by RPHPLC (acetonitrile/water 0.05% trifluoroacetic acid) to give 500 mg of a white powder: $^1$H NMR (d$_6$-DMSO) δ2.45 (m, 2H), 2.6 (m, 2H), 2.8 (m, 2H), 5.24 (m, 1H), 7.65 (m, 1H), 7.77 (m, 4H), 8.13 (m, 1H), 8.25 (m, 2H), 8.72 (bs, 1H), 9.18 (bs, 2H), 10.4 (s, 1H); MS (ES) m/e 384.1(MH+).

Elemental Analysis Required for $C_{19}H_{21}N_5O_4.2F_3C_2O_2H.0.5H_2O$: C 44.52 H 3.90 N 11.28 Found: C 44.59 H 3.79 N 11.24

EXAMPLE 3

β-[[4-[[3-(aminoiminomethyl)phenyl]amino]-1,5-dioxopentyl]amino]-3-pyridinepropanoic acid

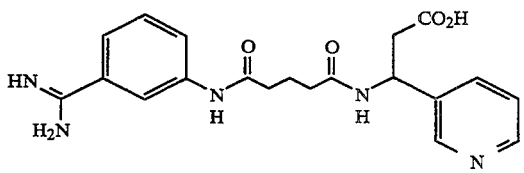

Step 1 Preparation of 4-[[3-(aminoiminomethyl)phenyl]amino]-5-oxopentanoic acid.

3-Aminobenzamidine di-HCL (5 g, 24 mmol) was added to dry DMF (30 mL). To this solution dry pyridine (5 mL) and glutaric anhydride (3.0 g, 26 mmol), followed by 10 mg dimethylaminopyridine (DMAP) were added. The product was heated for 3 h at 100° C. and allowed to stir at room temperature for 16 h. Solvents were removed in vacuo, water was added to the residue and the pH was brought to a value of 6.8 using dilute sodium hydroxide. An abundant precipitate was filtered, washed with water followed by ethyl acetate. The white solid was filtered and dried in a desiccator to give 5.4 g, 90% of product as a white solid: $^1$H NMR (d$_6$-DMSO) δ1.8 (m, 2H), 2.3 (m, 2H), 2.45 (m, 2H), 7.6 (d, 1H,J=8 Hz), 7.55 (dd, 1H,J=8 Hz and J=7.5 Hz), 7.85 (d, 1H,J=7.5 Hz), 8.05 (s, 1H), 9.05 (bs, 2H), 9.25 (bs, 2H), 10.4 (s, 1H); MS (FAB) m/e 250.1 (MH+).

Step 2 Preparation of ethyl β-[[4-[[3-(aminoiminomethyl)phenyl]amino]-1,5-dioxopentyl]amino]-3-pyridinepropanoate.

In a flask under nitrogen, the compound prepared above (Example 3, Step 1; 5.2 g) was activated as described in example 1, Step 2 and coupled with 1.87 g of ethyl β-amino-3-pyridinepropanoate dihydrochloride. After 1 h, the reaction mixture was concentrated in vacuo and the product purified by RPHPLC as described in Example 1 to give 0.7 g of ethyl β-[[4-[[3-(aminoiminomethyl)phenyl]amino]-1,5-dioxopentyl]amino]-3-pyridinepropanoate; $^1$H NMR (d$_6$-DMSO) δ1.5 (t, 3H,J=7 Hz), 1.8 (m, 2H), 2.35 (m, 4H), 2.95 (d, 1H, J=7 Hz), 4.05 (q, 2H, J=7 Hz), 5.4 (t, 1H, J=7 Hz), 7.45 (m, 2H), 8.0 (dd, 1H, J=8 Hz and J=7.5 Hz), 7.8 (s, 1H), 8.55 (d, 1H, J=8 Hz), 8.65 (d, 1H, J=7 Hz), 8.75 (s, 1H).

Step 3 Preparation of β-[[4-[[3-aminoiminomethyl)phenyl]amino]-1,5-dioxopentyl] amino]-3-pyridinepropanoic acid.

The ester isolated in Step 2 was dissolved in dilute ammonium hydroxide (pH=9.8) and stirred at 25° C. for 72 h. The resulting mixture was purified by RPHPLC. After lyophilization, 250 mg of slightly hygroscopic product was isolated: $^1$H NMR (d$_6$-DMSO) δ1.8 (m, 2H), 2.25 (m, 2H), 2.35 (m, 2H), 2.95 (d, 1H, J=7 Hz), 5.25 (m, 1H), 7.40 (m, 2H), 7.5 (d, 1H, J=8 Hz), 7.65 (t, 1H, J=8 Hz), 7.8 (d, 1H, J=8 Hz), 8.15 (m, 2H), 8.6 (d, 1H, J=8 Hz), 8.65 (d, 1H, J=7 Hz), 8.75 (s, 1), 10.25 (s, 1H); MS (FAB) m/e 398(MH+), 248.8.

Elemental Analysis Required for $C_{20}H_{23}N_5O_4 \cdot CF_3CO_2H.H_2O$: C 44.81 H 4.22 N 10.89 Found: C 44.68 H 4.02 N 10.82

EXAMPLE 4

Ethyl βS-[[4-[[4-(aminoiminomethyl)phenyl]amino]-1,4-dioxobutyl]amino]-3 -pyridinepropanoate

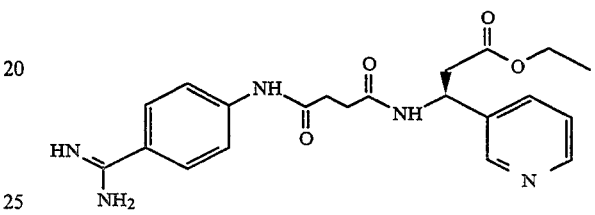

Step 1 Preparation of ethyl trans-3-(3-pyridyl) acrylate.

Trans-3-(3-pyridyl) acrylic acid (Aldrich, P6,620-3) was esterified with dry HCl in ethanol. After removal of the solvent in vacuo, the residue was partitioned between potassium carbonate and methylene chloride. The organic phase was dried and concentrated to provide the ester as a clear yellowish oil (yield >95%) and used without further purification. $^1$H NMR (d6-DMSO) δ1.34 (t, 3H, J=7.2 Hz), 4.27 (q, 2H, J=7.2 Hz), 6.5 (d, 1H, J=15 Hz), 7.32 (m, 1H), 7.67 (d, 1H, 16 Hz), 7.83 (m, 1H), 8.6 (m, 1H), 8.74 (bs, 1H).

Step 2 Preparation of ethyl-N-[(R)-1-phenylethyl]-(S)-3-amino-3-pyridyl propanoate.

Trimethylsilyl chloride (33.5 g, 0.33 mol) was added to (R)-(+)-α-methylbenzylamine (34 g, 0.28 mol) and triethylamine (40 g, 0.4 mol) in 100 ml of tetrahydrofuran. This mixture was allowed to stir for 1 h at 25° C. The triethylamine hydrochloride was filtered through a medium scintered glass funnel under a blanket of nitrogen. The resulting clear silylamine in tetrahydrofuran solution was cooled to −78° C. and n-BuLi (84 ml, 0.21 mol) was added. The anion was stirred for 15 min. followed by the addition of ethyl trans-3-(3pyridyl) acrylate (25 g, 0.14 mol) in 50 ml of tetrahydrofuran and the mixture stirred for 15 min at −78° C. before quenching with saturated ammonium chloride (100 ml). The mixture was allowed to warm and extracted with diethyl ether. This solution was concentrated to 60 ml, then 1N HCl was added and extracted with ether again. The ether extracts were discarded. The acidic solution was made basic with solid $K_2CO_3$, extracted with methylene chloride, and the organic layer was dried over $Na_2SO_4$. The solvent was removed under reduced pressure to afford a red oil. The product was purified on silica gel (30% ethyl acetate in hexane) to give 24 g of enantiomerically enriched amine as an amber oil. $^1$H NMR (d6-DMSO) δ1.17 (t, 3H, J=7.2 Hz), 1.35 (d, 3H, J=6.6 Hz), 2.69 (qd, 2H, J=6.22, 15 Hz), 3.66 (q, 1H, J=6.6, 15 Hz), 4.07 (q, 2H, J=7.2 Hz), 4.19 (t, 1H, J=7.31 Hz), 7.2 (m, 6H), 7.59 (dt, 1H, J=2 Hz, J=7.9 Hz), 8.45 (dd, 1H, J=2, J=4.7 Hz), 8.48 (d, 1H, J=2 Hz). MS (FAB) m/e 299.1. [α]D: +7.5° (cl.0, CHCl3).

Step 3 Preparation of ethyl-(S)-3-amino-3-pyridyl propanoate.

Procedure A The enantiomerically enriched amino-ester from Step 2 (6 g) was added to ethanol (150 ml), followed by the addition of ammonium formate (6 g) and palladium on carbon 10% (6 g). Additional ammonium formate and/or palladium/C may have to be added if reduction slows. The mixture was refluxed for 4 h. The progress of the reaction was monitored by tlc (chloroform/methanol10:1; Rf of product ~0.1). After complete reaction the mixture was filtered through a celite pad and the ethanol removed under reduced pressure. The product was purified by reverse phase chromatography (water/acetonitrile) to result in 1.5 g of amino ester TFA salt. $^1$H NMR (d6-DMSO) δ1.09 (t, 3H, J=7.1 Hz), 3.12 (m, 2H, J=8.48, 16.49, 19.31 Hz), 4.04 (m, 2H), 4.75 (t, 1H, J=6.9 Hz), 7.60 (dd, 1H, J=5.0, 8.0 Hz), 8.09 (dt, 1H, J=7.9, 8.0 Hz), 8.65 (dd, 1H, J=1.4, 4.9 Hz), 8.76 (d, 1H, J=1.9 Hz). [α]D +3.3° (c=1.0, DMF).

Procedure B A solution of the enantiomerically enriched aminoester (8.2 g) in 25 mL of 1,4-cyclohexadiene and 100 mL of glacial acetic acid was treated with 8 g of 5% Pd on carbon. The mixture was heated for 4 h at 70°-75° C. under nitrogen. The reaction was monitored by HPLC. After cooling, the reaction mixture was filtered through a celite pad and was concentrated in vacuo. The resulting clear oil was triturated with 3×50 mL diethylether which was then decanted. The oil was dissolved in 250 mL water and 4 mL trifluoroacetic acid and the solution purified as above. The appropriate fractions were combined to give 8.1 g (68%) of the di-TFA salt. The ratio of the enantiomers was determined to be 5.3:94.7/R:S using a CrownPak CR (+) column.

Step 2 Preparation of ethyl βS-[[4-[[4-(aminoiminomethyl)phenyl]amino]-1,4-dioxobutyl]amino]-3-pyridinepropanoate.

In a flask under nitrogen, 4-succinylamido benzamidine. HCL prepared in Example 1, Step 1 (5 g) was added to dry DMF (200 ml) followed by N-methylmorpholine (2.52 mL) and isobutyl chloroformate (2.85 mL) at 25° C. The mixture was stirred for 5 min. (S)-β-Amino-3-pyridinepropionic acid ethyl ester ditrifluoroacetate (7.73 g) in solution in a mixture of 100 mL DMF, 4 mL N-methylmorpholine and 100 mg DMAP was added over a period of 5 min. After 1 h at room temperature, water was added and the reaction concentrated in vacuo. The residue was triturated with ether (3×25 mL), then dissolved in water and the pH adjusted to 6.7. A precipitate was filtered off. The filtrate pH was adjusted to 1 with TFA and was purified by reverse phase chromatography (water/acetonitrile) to give 7.3 g of white solid (52% yield). A portion of the solid (3.5 g) was dissolved in water and the trifluoroacetate ion was exchanged for acetate using 10 equivalents of resin AG1X-8 (acetate form, Biorad). The aqueous solution resulting from the exchange was lyophilized to a colorless powder (2.5 g): $^1$H NMR (DMSO) δ1.1 (t, 3H, J=7 Hz), 1.7 (s, 3H), 2.4 (m, 2H), 2.5 (m, 4H), 2.8 (d, 1H, J=7 Hz), 3.95 (q, 2H, J=7 Hz), 5.2 (m, 1H), 7.3 (m, 1H), 7.7 (m, 4H), 8.4 (dd, 1H, J=8 Hz and J=2.5 Hz), 8.5 (d, 1H, J=2.5 Hz), 8.55 (d, H, J=8 Hz). [α]D −1.32° (c=0.5, H2O).

Elemental Analysis Required for C23H29N5O6.H2O: C 56.46 H 6.34 N 14.30 Found: C 56.69 H 6.06 N 14.32

EXAMPLE 5

βS-[[4-[[4-(aminoiminomethyl)phenyl]amino]-1,4-dioxobutyl]amino]-3-pyridinepropanoic acid

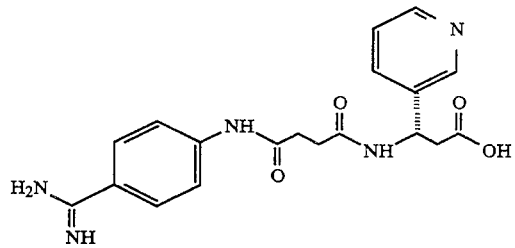

A portion (100 mg) of the ester isolated in Example 4 was dissolved in water and 2N aqueous LiOH was added to pH 12. After stirring one hour at 25° C., the resulting mixture was purified by reverse phase high pressure chromatography (Rt=8 min on linear gradient 5-70% ACN in water over 30 min). After lyophilization, 90 mg of white solid was isolated: $^1$H NMR (DMSO) δ2.5 (m, 2H), 2.55 (m, 2H), 2.8 (m, 2H), 5.25 (m, 1H), 7.40 (m, 2H), 7.5 (bs, 1H), 7.75 (s, 4H), 7.95 (bs, 1H), 8.15 (m, 2H), 8.6 (m, 2H), 8.95 (bs, 2H), 9.15 (bs, 2H), 10.45 (s, 1H); MS (FAB) m/e 384(MH+). [α]D: −1.15° (c 1.0, DMSO).

Elemental Analysis Required for C20H23N5O4.1.52F3CO2H.1/2H2O; C 47.24 H 4.45 N 12.89 Found: C 46.9 H 4.2 N 12.43

EXAMPLE 6

βR-[[4-[[4-(aminoiminomethyl)phenyl]amino]-1,4-dioxobutyl]amino]-3-pyridinepropanoic acid

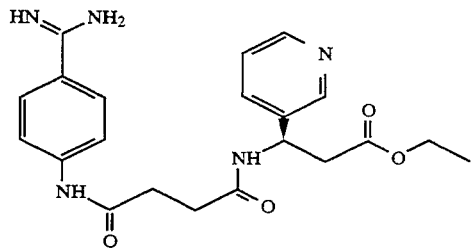

Step 1 Preparation of ethyl-N-[(S)-1-phenylethyl]-(R)-3-amino-3-pyridyl propanoate.

Trimethylsilyl chloride (33.5 g, 0.33 mol) was added to (S)-(−)-α-methylbenzylamine (34 g, 0.28 mol) and triethylamine (40 g, 0.4 mol) in 100 ml of tetrahydrofuran. This mixture was allowed to stir for 1 h at 25° C. The triethylamine hydrochloride was filtered through a medium scintered glass funnel under a blanket of nitrogen. The resulting clear silylamine in tetrahydrofuran solution was cooled to −78° C. and n-BuLi (84 ml, 0.21 mol) was added. The anion was stirred for 15 min. followed by the addition of ethyl trans-3-(3-pyridyl)acrylate (25 g, 0.14 mol) in 50 ml of tetrahydrofuran and the mixture stirred for 15 min at −78° C. before quenching with saturated ammonium chloride (100 ml). The mixture was allowed to warm and extracted with diethyl ether. This solution was concentrated to 60 ml, then 1N HCl was added and extracted with ether again. The ether extracts were discarded and the acidic solution was made basic with solid K2CO3, extracted with methylene chloride, and the organic layer was dried over Na₂SO₄. The solvent was removed under reduced pressure to a red oil. The product was purified on silica gel (30% ethyl acetate in hexane) to give 24 g of enantiomerically enriched amine as an amber oil. ¹H NMR (d6-DMSO) δ1.17 (t, 3H, J=7.2 Hz), 1.35 (d, 3H, J=6.6 Hz), 2.69 (qd, 2H, J=6.22, 15 Hz), 3.66 (q, 1H, J=6.6, 15 Hz), 4.07 (q, 2H, J=7.2 Hz), 4.19 (t, 1H, J=7.31 Hz), 7.2 (m, 6H), 7.59 (dt, 1H, J=2 Hz, J=7.86 Hz), 8.45 (dd, 1H, J=2, J=4.74 Hz), 8.48 (d, 1H, J=2 Hz). MS (FAB) m/e 299.1. [α]D: −7.5° (c1.0, CHCl3).

Step 2 Preparation of ethyl-(R)-3-amino-3-pyridyl propanoate.

The enantiomerically enriched aminoester from Step 1 (9 g) was added to ethanol (150 ml) followed by the addition of ammonium formate (10 g) and palladium on carbon 10% (10 g). Additional ammonium formate and/or palladium/C may have to be added if reduction slows. The mixture was stirred at 60° C. for 6 hr. The progress of the reaction was monitored by tlc (chloroform/methanol-10:1; Rf of product ~0.1). After complete reaction the mixture was filtered through a celite pad and the ethanol removed under reduced pressure. The product was purified by reverse phase chromatography (water/acetonitrile) to result in 1.5 g of amino ester TFA salt. The ratio of the enantiomers was determined to be 6:94/S: R using a CrownPak CR (+) column.¹H NMR (d6-DMSO) δ1.09 (t, 3H, J=7.10 HZ), 3.12 (m, 2H1, 4.04 (m, 2H), 4.75 (t, 1H, J=6.87 Hz), 7.60 (dd, 1H, J=5.0, 8.0 Hz), 8.09 (dt, 1H, J=7.8, 8.0 Hz), 8.65 (dd, 1H, J=1.4, 4.9 Hz), 8.76 (d, 1H, J=1.9 Hz). [α]D: +3.3° (cl. 0, DMF).

In a flask under nitrogen, Y-succinylamido-benzamidine-HCL prepared in Example 1, Step 1 (465 mg, 1.6 mmol) was added to dry DMF (50 ml) followed by N-methylmorpholine (0.18 mL) and isobutyl chloroformate (0.22 mL) at 25° C. The mixture was stirred for 5 min. Ethyl β(R)-Amino-3-pyridinepropoate acid ethyl ester ditrifluoroacetate (650 mg) in solution in a mixture of 50 mL DMF, 0.6 mL N-methylmorpholine was added at once. After 1 h at room temperature, water was added and the reaction concentrated in vacuo. The residue was purified by reverse phase chromatography (water/acetonitrile 0.05% trifluoroacetic acid) to give 350 mg of white solid: 1H NMR (DMSO) 6 1.1 (t, 3H, J=7 Hz), 1.7 (s, 3H), 2.4 (m, 2H), 2.5 (m, 4H), 2.8 (d, 1H, J=7 Hz), 3.95 (q, 2H, J=7 Hz), 5.2 (m, 1H), 7.3 (m, 1H), 7.7 (m, 4H), 8.4 (dd, 1H, J=8 Hz and J=2.5 Hz), 8.5 (d, 1H, J=2.5 Hz), 8.55 (d, 1H, J=8 Hz). [α]D: +1.4° (c 0.5 H₂O).

EXAMPLE 7

βR-[[4-[[4-(aminoiminomethyl)phenyl]amino]-1,4-dioxobutyl]amino]-3-pyridinepropanoic acid

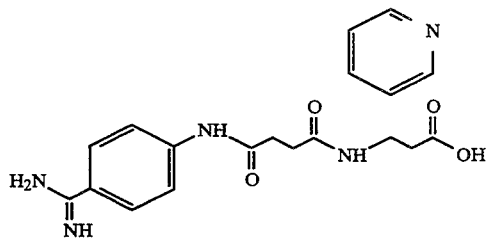

A portion (100 mg) of the ester isolated in Example 6 was dissolved in water and 2N aqueous LiOH was added to pH 12. After stirring one hour at 25° C., the resulting mixture was purified by reverse phase high pressure chromatography (Rt=8 min on linear gradient 5–70% ACN in water over 30 min). After lyophilization, 90 mg of white solid was isolated: ¹H NMR (DMSO) δ2.5 (m, 2H), 2.55 (m, 2H), 2.8 (m, 2H), 5.25 (m, 1H), 7.40 (m, 2H), 7.5 (bs, 1H), 7.75 (s, 4H), 7.95 (bs, 1H), 8.15 (m, 2H), 8.6 (m, 2H), 8.95 (bs, 2H), 9.15 (bs, 2H), 10.45 (s,1H); MS (FAB) m/e 384(M+H+). [α]D: +1.12 ° (c 1.0, DMSO).

Elemental Analysis Required for C₂₀H₂₃N₅O₄.1F₃.C₂O₂H.H₂O: C 43.88 H 4.00 N 11.12 Found: C 43.84 H 3.51 N 10.79

EXAMPLE 8

β-[[4-[[4-(aminoiminomethyl)phenyl]-amino]-1,4-dioxobutyl]-2-pyridinepropanoic acid

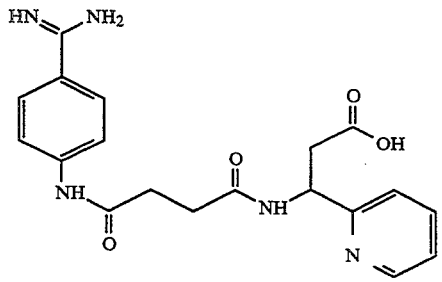

Step 1 Preparation of ethyl 2-pyridylmalonate.

Diethyl malonate (15 g, 93.5 mmol), 2-pyridylcarboxaldehyde (10 g, 93.5 mmol), piperidine (1 g) benzoic acid (1 g) were all added to benzene (200 ml) heated in a flask fitted with a Dean-Stark trap to remove water. After 24–48 h, the reaction was complete and the benzene removed in vacuo. The resulting oil was distilled 270° C. @1 mm Hg to give 18 g of unsaturated diester. 1H NMR (300 MHz) (d6-DMSO) δ1.35 (m, 6H), 4.35 (q, 2H, J=7.8 Hz), 4.4 (q, 2H, J=4.4 Hz), 7.21 (m, 1H), 7.4 (m, 1H), 7.6 ( s, 1H), 7.7 (m, 1H), 8.6 (m, 1H); MS (FAB) m/e (MH+) 250.3.

Step 2 Preparation of ethyl ethoxycarbonyl-3-amino-3-(2-pyridyl) propanoate.

Ammonia saturated methanol (75 ml) was added to the unsaturated diester (5 g) above in dioxane (25 ml) and left to stand for 1 h. After complete reaction the excess ammonia in methanol was removed under reduced pressure. FAB (MH+) 267.2

Step 3 Preparation of β-[[4-[[4-aminoiminomethyl) phenyl]-amino]-1,4-dioxobutyl]2-pyridinepropanoic acid.

4-[[4-(Aminoiminomethyl)phenyl]-amino]-4-oxobutanoic acid hydrochloride prepared in Example 1, Step 1 (5.0 g, 18.5 mmol) was added to dry DMF (250 ml) followed by N-methylmorpholine (1.9 g, 18.5 mmol) and isobutyl chloroformate (2.5 g, 18.5 mmol) at 25° C. The mixture was stirred for 5 min. 3-amino diethyl ester from step 2 (5.0 g, 17 mmol) was added followed by dimethylaminopyridine. After 1 h, the solvent was removed under reduced pressure and the product purified by reverse phase chromatography (water/acetonitrile) to result in 6.0 g of a white solid. This material was hydrolyzed with LiOH (1 g) in water/acetonitrile. After complete conversion to the diacid, 6N HCl was added followed by warming to 80° C. for 1 h. The monoacid was purified by reverse phase chromatography (water/acetonitrile) to result in 3.0 g of a white solid ¹H NMR (d6-DMSO) 6 2.4 (m, 2H), 2.67 (m, 2H), 2.75 (ddd, 2H, J=6.6, 7.6, 16.1 Hz), 4.72 (m, 1H), 7.3 (m, 1H), 7.4 (m, 1H), 7.79 (s, 4H), 7.99 (d, 1H, J=8.1 Hz), 8.99 (m, 2H), 9.1 (bs, 2H), 9.19 (bs, 2H), 10.42 (s, 1H); MS (FAB) m/e 384.2 (MH+).

Elemental Analysis Required for C19H4O4H2 . H2O: C43.88 H 3.97 N 11.33 Found: C 43.65 H 3.54 N 10.87

EXAMPLE 9

Ethyl-β-[[4-[[4-(aminoiminomethyl)phenyl]amino]-1,4-dioxobutyl]-2-pyridinepropanoate

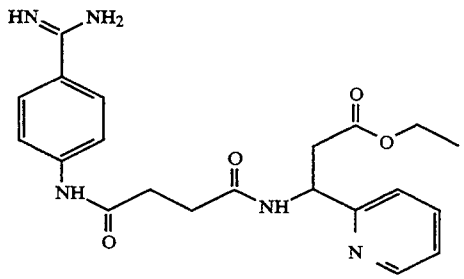

β-[[4-[[4-(aminoiminomethyl)phenyl]-amino]-1,4-dioxobutyl]-2-pyridine propanoic acid (1.2 g) from the step 3 from Example 8 was added to ethanol (70 ml) followed by 4N HCl/dioxane (10 ml). The course of the reaction was monitored by RPHPLC. After complete reaction (2 h), the product was purified by reverse phase chromatography (water/acetonitrile) to result in 930 mg of a white solid: 1H NMR (d6-DMSO) δ1.13 (t, 3H, J=7.8 Hz), 2.4 (m, 2H), 2.67 (m, 2H), 2.75 (ddd, 2H, J=6.6, 7.6, 16.12 Hz), 4.1 (q, 2H, J=7.8 Hz), 5.32 (m, 1H), 7.3 (m, 1H), 7.4 (m, 1H), 7.79 (s, 4H), 7.99 (d, 1H, J=8.1 Hz), 8.99 (m, 2H), 9.1 (bs, 2H), 9.19 (bs, 2H), 10.42 (s, 1H); MS (FAB) m/e 412.1 (MH+).

Elemental Analysis Required for C21H25N5O4 .1.5F3C2O2H . H2O0 c 46.61 H 4.53 N 11.32 Found C 46.49 H 4.37 N 10.43

EXAMPLE 10

β-[[4-[[4-(aminoiminomethyl)phenyl]-amino]-1,4-dioxobutyl]-4-pyridinepropanoic acid

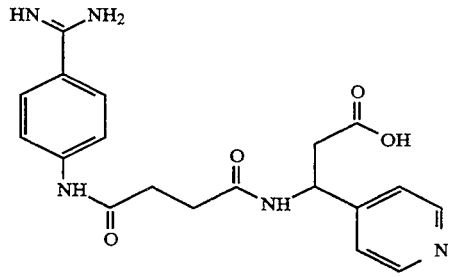

Step 1 Preparation of ethyl (4-pyridyl)malonate Diethyl malonate (15 g, 93.5 retool), 4-pyridylcarboxaldehyde (10 g, 93.5 mmol), piperidine (1 g) benzoic acid (1 g) were all added to benzene (200 ml) heated in a flask fitted with a Dean-Stark trap to remove water. After 24-48 h, the reaction was complete and the benzene removed in vacuo. The resulting oil was distilled 250° C. @1 mm Hg to give 23 g of unsaturated diester. 1H NMR (300 MHz) (d6-DMSO) δ1.25 (t, 3H, J=7.6 Hz), 1.32 (t, 3H, J=7.6 Hz), 4.3 (m, 4H), 7.31 (m, 2H), 7.64 (s, 1H), 8.65 (m, 2H); MS (FAB) m/e (MH+): 250.1.

Step 2 Preparation of ethyl ethoxycarbonyl-3-amino-4-pyridyl propanoate. Ammonia saturated methanol (75 ml) was added to the unsaturated diester (5 g) above in dioxane (25 ml) and left to stand for 1 h. After complete reaction the excess ammonia in methanol was removed under reduced pressure. FAB (MH+): 267.3

Step 3 Preparation of β-[[4-[[4-aminoiminomethyl) phenyl]-amino]-1,4-dioxobutyl]-4-pyridinepropanoic acid.

4-[[4-(aminoiminomethyl)phenyl]-amino]-4-oxobutanoic acid hydrochloride prepared in Example 1, Step 1 (5.0 g, 18.5 mmol) was added to dry DMF (250 ml) followed by N-methylmorpholine (1.9 g, 18.5 mmol) and isobutyl chloroformate (2.5 g, 8.5 mmol) at 25° C. The mixture was stirred for 5 min. 3-amino diethyl ester from step 2 (5.0 g, 17 mmol) was added followed by dimethylaminopyridine. After 1 h, the solvent was removed under reduced pressure and the product purified by reverse phase chromatography (water/acetonitrile) to result in 6.0 g of a white solid. This material was hydrolyzed with LiOH (1 g) in water/acetonitrile. After complete conversion to the diacid, 6N HCl was added followed by warming to 80° C. for 1 h. The monoacid was purified by reverse phase chromatography (water/acetonitrile) to result in 3.0 g of a white solid 1H NMR (d6-DMSO) δ2.5 (m, 2H), 2.6 (m, 2H), 2.85 (m, 2H), 5.26 (m, 1H), 7.63 (m, 2H), 7.79 (s, 4H), 8.6 (d, 1H, J=8.1 Hz), 8.67 (m, 2H), 8.99 (bs, 2H), 9.19 (bs, 2H), 10.42 (s, 1H); MS (FAB) m/e 384.2 (MH+).

Elemental Analysis Required for C19H21N5O4 . F6C4O4H2 . H2O: C 43.88 H 3.97 N 11.13 Found: C 43.65 H 3.54 N 10.87

EXAMPLE 11

Ethyl-β-[[4-[[4-(aminoiminomethyl)phenyl]amino]-1,4-dioxobutyl]-4-pyridinepropanoate

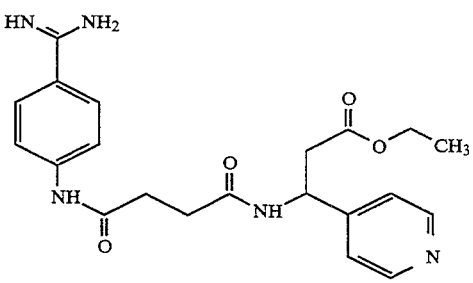

3-[[4-[[4-(aminoiminomethyl)phenyl]-amino]-1,4-dioxobutyl]-3-(4-pyridyl) propanoate (1.2 g) from the previous example—step 3 was added to ethanol (70 ml) followed by 4N HCl/dioxane (10 ml). The course of the reaction was monitored by RPHPLC. After complete reaction (2 h), the product was purified by RPHPLC (water/acetonitrile 0.05% trifluoroacetic acid) to result in 930 mg of a white solid: 1H NMR (d6-DMSO) δ1.13 (t, 3H, J=7.6 Hz), 2.4 (m, 2H), 2.67 (m, 2H), 2.75 (m, 2H), 4.1 (m, 2H), 5.32 (m, 1H), 7.3 (m, 1H), 7.4 (m, 1H), 7.79 (s, 4H), 7.99 (d, 1H, J=8.1 Hz), 8.99 (m, 2H), 9.1 (bs, 2H), 9.19 (bs, 2H), 10.42 (s, 1H); MS (FAB) m/e 412.3 (MH+).

Elemental Analysis Required for C21H25N5O4 .1.5F3C2O2H . H2O: C 46.61 H 4.53 N 11.32 Found: C 46.49 H 4.37 N 10.43

EXAMPLE 12

Ethyl β-[[[2-[[[4-aminoiminomethyl)phenyl]amino]carbonyl]cyclopropyl]carbonyl]amino]-3-pyridinepropanoate, bis(trifluoroacetate)

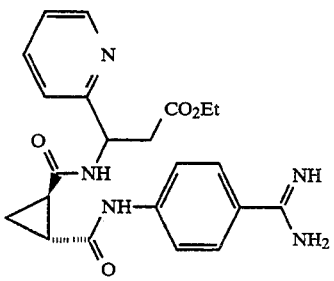

Step 1 Preparation of ethyl [2-[[[4-(aminoiminomethyl)-phenyl]amino]carbonyl]cyclopropyl]carboxylate.

Diethyl cyclopropyl carboxylate (25 g; trans isomer from Aldrich) was added to a solution of 5.65 g LiOH in 50 mL H₂O. The two phase mixture was stirred and 50 mL ethanol was added. After 5 min stirring, a yellow homogeneous mixture was observed and stirring continued for 24 h at 25° C. The crude reaction mixture was partitioned between ethyl acetate and water (pH=9). Then the aqueous layer was made acrdic (pH2), and extracted with ethyl acetate. The ethyl acetate extract contained 15 g of a mixture 2:1 of monoethyl ester: diacid. A portion of this mixture (7.5 g) was suspended in dichloromethane and treated with a total of 67 mL oxalyl chloride at room temperature for a total time of 20 h. After concentration in vacuo, the residual oil was taken up in 20 mL dimethylformamide and a mixture of aminobenzamidine dihydrochloride (12.5 g, 0.06 mol) and 15 mL of triethylamine in 50 mL dimethylformamide was added slowly. After 16 hr stirring at 25° C., the reaction was concentrated and the residue taken up in H₂O/acetonitrile and purified by RPHPLC. The major peak (detection at 225 nM) was collected (Rt on a linear H2O:ACN 5:95-70:30 over 25 min is 16 min). Lyophilization gave 730 mg of a white powder; MS (FAB) m/e 276.2 (MH+).

Step 2 Preparation of 2-[[[4-aminoiminomethyl) phenyl]amino]carbonyl]cyclopropyl-carboxylic acid.

The product prepared above was stirred in a solution of 1 g LiOH, 5 mL acetonitrile and 10 mL H₂O for 6 h at room temperature. A precipitate appeared upon adjusting the pH to 6 and upon concentration. The precipitate was collected, redissolved in H₂O:acetonitrile and pH brought to 2 with HCl. This solution after lyophilization gave 480 mg of white solid: ¹H NMR (CD₃OD) δ1.3 (m, 2H), 1.95 (m, 1H), 2.12 (m, 1H), 7.6 (m, 4H).

Step 3 Preparation of ethyl[[[2-[[[4-(aminoiminomethyl)phenyl]amino]carbonyl]cyclopropyl]carbonyl]amino]-3-pyridinepropanoate, bis(trifluoroacetate).

The acid prepared in step 2 (480 mg, 1.7 mmol) was coupled to 534 mg (2 mmol) of ethyl β-amino-3-pyridinepropoponoate acid ethyl ester dihydrochloride using the mixed anhydride procedure in the manner described in Example 7. After concentration in vacuo, the residue was purified by RPHPLC (H₂O:ACN:0.05%TFA) and a peak eluting at 12.5 min (Rt on a linear H₂O(0.05% TFA):ACN 5:95-70:30 over 25 min) was collected which after lyophilization provided 80 mg of white solid: ¹H NMR (DMSO) δ1.12 (t, 3H, J=7 Hz), 1.25 (m, 2H), 2.16 (m, 2H), 2.85 (m, 2H), 3.95 (q, 2H, J=7 Hz), 5.28 (m, 1H), 7.65 (m, 4H), 8.09 (d, 1H, J=8 Hz), 8.5 (m, 3H), 8.65 (bs, 2H), 9.0 (d, 0.8H, J=8 Hz); MS (FAB) m/e 24.1(MH+).

EXAMPLE 13

Preparation of [[[2-[[[4-aminoiminomethyl)phenyl]amino]carbonyl]cyclopropyl]carbonyl]amino]-3-pyridinepropanoic acid, bis(trifluoroacetate)

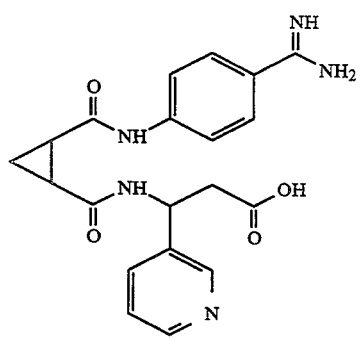

A mixture of the ester from Step 3—Example 12 (80 mg), 50 mg LiOH, 25 mL H₂O, 5 mL acetonitrile were stirred at room temperature for 90 min. After acidification to pH 2, the mixture was purified by RPHPLC. The main peak was collected and lyophilized to afford 60 mg of a white powder: MS (FAB) m/e 396.2.1(MH+).

Elemental Analysis Required for C₂₄H₁₇N₄O₄.F₆C₄H₂.1.5H₂O: C 44.31 H 4.02 N 10.76 Found: C.44.35 H 3.62 N 10.78

EXAMPLE 14

β-[[[2-[[[4-aminoiminomethyl)phenyl]amino]carbonyl]-cyclohexyl]carbonyl]amino]-3-pyridinepropanoic acid, bis(trifluoroacetate)

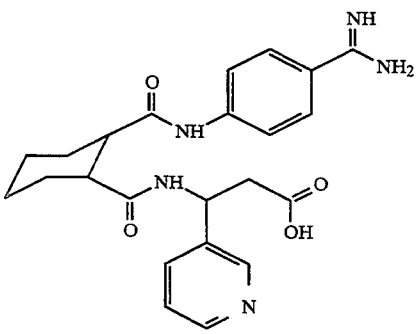

Step 1 β-[[[2-[[[4-aminoiminomethyl) phenyl]amino]-carbonyl]cyclohexyl]carboxylic acid.

A mixture of 10 g trans-1,2-cyclohexane-dicarboxylic anhydride (0,065 mol), 13.7 g (0,065 mol) aminobenzamidine dihydrochloride, 100 mL of pyridine and 100 mL of dimethylformamide was stirred at 100° C. for 3 h.

The reaction mixture was concentrated in vacuo, brought to pH 7 with sodium hydroxide (0.5N) and water (total volume 200 mL). Upon cooling, a precipitate formed which was filtered (14 g): ¹H NMR (DMSO) δ1.3 (bs, 4H), 1.75 (bs, 2H), 2.2 (bs, 2H), 2.5 (bs, 2H), 7.8 (s, 4H), 9.1 (bs, 2H), 9.2 (bs, 2H); 10.4 (s, 1H); MS (FAB) m/e 290.1 (MH+). The material was dissolved in aqueous HCl (0.2N) and lyophilized to a white powder.

Step 2 β-[[[2-[[[4-aminoiminomethyl)phenyl] amino]-carbonyl]cyclohexyl]carbonyl]amino]-3-pyridine-propanoic acid, bis(trifluoroacetate).

The acid prepared in step 1 (1.3 g, 4 mmol) was coupled to 1.06 g (4 mmol) of ethyl β-amino-3-pyridine-propanoate dihydrochloride using the mixed anhydride procedure in the manner in Example 7. After concentration in vacuo, the residue was purified by RPHPLC (H₂O:ACN:0.05%TFA) and a peak eluting at 14.5 min (Rt on a linear H₂O:ACN 5:95–70:30 over 25 min) was collected which after lyophilization provided 300 mg of white solid: MS (FAB) m/e 466.1 (MH+). This material was stirred in 10 mL 2N LiOH for 2 h at 25° C. The final product was purified by RPHPLC and provided 70 mg of white powder upon lyophilization:¹H NMR (DMSO) δ1.25 (m, 4H), 1.85 (m, 2H), 1.95 (m, 2H), 2.6 (m, 2H), 2.85 (m, 2H),, 5.2 (m, 1H), 7.4 (m, 1H), 7.75 (m, 4H), 8.09 (d, 1H, J=7.5 Hz), 8.5 (m, 1H), 8.6 (d, 1H, J=7.5 Hz), 8.65 (s, 1H), 8.9 (bs, 2H), 9.15 (d, 0.8H, J=8 Hz), 10.25 (s, 1H).

Required for $C_{23}H_{27}N_5O_4 \cdot F_6C_4O_4H_2 \cdot H_2O$: C 47.44 H 4.57 N 10.52 Found: C. 47.73 H 4.62 N 10.16

EXAMPLE 15

Ethyl
β-[[4-[[4-(aminoiminomethyl)phenyl]amino]-1,4-dioxobutyl]amino-]-2-furanpropanoate

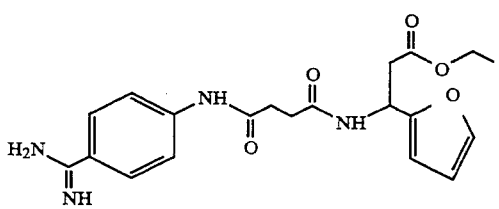

Step 1 Preparation of ethyl-3-amino-3-furanyl propanoate:

Ethyl hydrogen malonate (13.7 g, 104 mmol) was added to 2-furanal (10 g, 104 mmol) and ammonium acetate (20 g, 260 mmol) in dry ethanol. The solution was heated to reflux for 6 h. The solvent was removed in vacuo to leave an oil. To this oil, 10% HCl (250 mL) was added along with ether (100 mL). The layers were separated, extracted twice with methylene chloride, dried over Na₂SO₄, and the solvent removed in vacuo to give 6 g of the title compound.

Step 2 Preparation of ethyl β-[[4-[[-4-(aminoiminomethyl)phenyl]-amino]-1,4-dioxobutyl]amino]-2-furanpropanoate.

4-[[4-(aminoiminomethyl)phenyl]-amino]-4-oxobutanoic acid hydrochloride prepared in Example 1, Step 1 (4.6 g, 17 mmol) was added to dry DMF (225 ml) followed by N-methylmorpholine (1.2 g, 17 mmol) and isobutyl chloroformate (2.3 g, 17 mmol) at 25° C. The mixture was stirred for 5 min. Ethyl-3-amino-3-(2-furanyl) propanoate (3.1 g, 17 mmol) was added followed by dimethylaminopyridine. After 1 h, the solvent was removed under reduced pressure and the product purified by RPHPLC (water.05%TFA/acetonitrile) to afford in 3.0 g of a white solid: ¹H NMR (d6-DMSO) δ1.13 (t, 2H, J=7.5 Hz), 2.49 (m, 2H), 2.6 (m, 2H), 2.75 (m, 2H), 4.03 (q, 2H, J=7.5 Hz), 5.3 (m, 1H), 6.22 (m, 1H), 6.37 (m, 1H), 7.55 (m, 1H), 7.78 (s, 4H), 8.4 (d, 1H, J=8.1 Hz), 9.0 (bs, 2H), 9.17 (bs, 2H), 10.42 (s, 1H); MS (FAB) m/e 401.2 (MH+).

Elemental Analysis Required for $C_{20}H_{24}N_4O_5 \cdot F_3C_2O_2H \cdot H_2O$: C 51.86 H 5.86 N 10.89 Found: C 51.04 H 5.58 N 10.70

EXAMPLE 16

β[[4-[[4-(aminoiminomethyl)phenyl]amino]-1,4-dioxobutyl]amino]-2-furanpropanoic acid

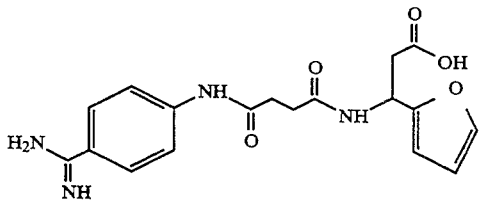

Ethyl β-[[4-[[4-(aminoiminomethyl)phenyl]amino]-1,4-dioxobutyl]amino-]-2-furan propanoate prepared in Example 17 (700 mg) was added to water/acetonitrile (20 ml) followed by lithium hydroxide (100 mg) at 25° C. The mixture was stirred for 30 min. The course of the reaction was monitored by RPHPLC. After satisfactory acid was formed the reaction was neutralized with TFA and purified by reverse phase chromatography (water/acetonitrile) to result in 620 mg of a white solid: ¹H NMR (d6-DMSO) δ2.49 (m, 2H), 2.6 (m, 2H), 2.75 (m, 2H), 5.27 (m, 1H), 6.22 (m, 1H), 6.37 (m, 1H), 7.55 (m, 1H), 7.78 (s, 4H), 8.35 (d, 1H, J=8.1 Hz), 9.0 (bs, 2H), 9.17 (bs, 2H), 10.42 (s, 1H); MS (FAB) m/e 373.5 (MH+).

Elemental Analysis Required for $C_{18}H_{20}N_4O_5 \cdot F_3C_2O_2H \cdot H_2O$: C 47.62 H 4.56 N 11.11 Found: C 47.24 H 4.98 N 11.67

EXAMPLE 17

Ethyl
β-[[4-[[4-(aminoiminomethyl)phenyl]amino]-1,4-dioxobutyl]amino-]-2-thiophenepropanoate

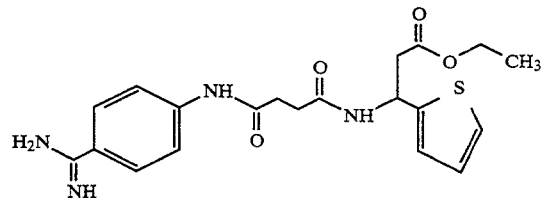

Step 1 Preparation of ethyl-3-amino-3-(2-thiophenyl) propanoate.

Ethyl hydrogen malonate (13.7 g, 104 mmol) was added to 2-thiophencarboxaldehyde (11.6 g, 104 mmol) and ammonium acetate(20 g, 260 mmol) in dry ethanol. The solution was heated to reflux for 6 h. After this time the solvent was removed under reduced pressure to leave an oil. To this oil 10% HCl (250 ml) was added along with ether (100 ml). The layers were separated and the aqueous layer was made basic with K₂CO₃ then extracted twice with methylene chloride, dried over Na₂SO₄ and solvent removed in vacuo to give 8 g of a yellow oil: ¹H NMR (300 MHz) (d6-DMSO) δ1.25 (t, 3H, J=7.7 Hz), 1.85 (bs, 2H), 2.7 (ddd, 2H, J=4.2, 9.1, 14.4 Hz), 4.18 (q, 2H, J=7.7 Hz), 4.68 (m, 1H), 7.14 (m, 1H), 7.3 (m, 1H), 7.6 (m, 1H); MS (FAB) m/e (MH+): 200.4.

Step 2 Preparation of ethyl β-[[4-[[4-(aminoiminomethyl)phenyl]-amino]-1,4-dioxobutyl]amino-]-2-thiophenepropanoate.

4-[[4-(Aminoiminomethyl)phenyl]-amino]-4-oxobutanoic acid hydrochloride prepared in Example 1, Step 1 (4.6 g, 17 mmol) was added to dry DMF (225 ml) followed by N-methylmorpholine (1.2 g, 17 mmol) and isobutyl chloroformate (2.3 g, 17 mmol) at 25° C. The mixture was stirred for 5 min. Ethyl-3-amino-3-(2-thiophenyl)propanoate (3.4 g, 17 mmol) was added followed by dimethylaminopyridine. After 1 h, the solvent was removed under reduced pressure and the product purified by RPHPLE (water/acetonitrile) to result in 3.3 g of a white solid: $^1$H NMR (d6-DMSO) δ1.12 (t, 2H, J=7.7 Hz), 2.49 (m, 2H), 2.6 (m, 2H), 2.75 (m, 2H), 4.03 (m, 2H), 5.48 (m, 1H), 6.95 (m, 2H), 7.48 (m, 1H), 7.78 (s, 4H), 8.55 (d, 1H, J=8.1 Hz), 9.0 (bs, 2H), 9.17 (bs, 2H), 10.42 (s, 1H); MS (FAB) m/e 417.1 (MH+).

Elemental Analysis Required for $C_{20}H_{24}N_4O_4S$. $F_3C_2O_2H \cdot H_2O$: C 49.81 H 4.72 N 10.57 Found: C 49.71 H 4.67 N 10.53

EXAMPLE 18

β-[[4-[[4-(aminoiminomethyl)phenyl]amino]-1,4-dioxobutyl]amino]-2-thiophenepropanoic acid

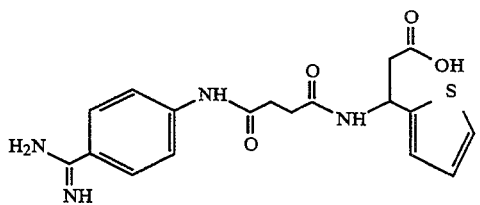

Ethyl 3-[[4-[[4-(aminoiminomethyl)phenyl]amino]-1,4-dioxobutyl]amino-]-3-(2-thiophenyl) propanoate prepared in Example 17, Step 2 (700 mg) was added to water/acetonitrile (20 ml) followed by lithium hydroxide (100 mg) at 25° C. The mixture was stirred for 30 min. The course of the reaction was monitored by RPHPLC. After satisfactory acid was formed the reaction was neutralized with TFA and purified by reverse phase chromatography (water/acetonitrile) to result in 620 mg of a white solid: $^1$H NMR (d6-DMSO) δ2.49 (m, 2H), 2.6 (m, 2H), 2.75 (m, 2H), 5.40 (m, 1H), 6.95 (m, 2H), 7.48 (m, 1H), 7.78 (s, 4H), 8.55 (d, 1H,J=8.1 Hz), 9.0 (bs, 2H), 9.17 (bs, 2H), 10.42 (s, 1H); MS (FAB) m/e 389.1 (MH+).

Elemental Analysis Required for $C_{18}H_{20}N_4O_4S$. $F_3C_2O_2H \cdot H_2O$: C 46.15 H 4.42 N 10.77 Found: C 46.44 H 4.11 N 10.77

EXAMPLE 19

Ethyl β-[[4-[[4-aminoiminomethyl)phenyl]amino]-1,4-dioxobutyl]amino]-1,3-benzodioxole-5-propanoate

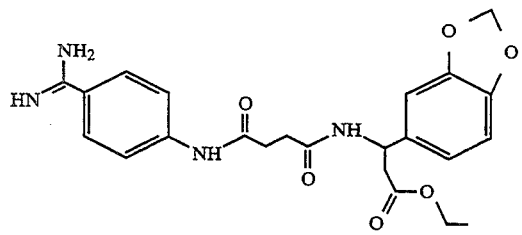

Step 1 Preparation of Ethyl β-amino-1,3-benzodioxole-5-propanoate.HCl.

3,4 methylenedioxybenzaldehyde (6.0 g; 40 mmole), malonic acid (5.2 g; 50 mmoles) and ammonium acetate (4 g; 52 mmoles) were gently refluxed in ethanol (350 ml) overnight. The reaction mixture was allowed to cool down to room temperature and the solid precipitate was collected by filtration and washed with ethanol/water (1:1;2×100 ml). The air dried free acid (3 g) [FAB-MS: MH+ =210] was suspended in the absolute ethanol (200 ml). The solution was cooled in an ice bath and bubbled with dry HCl gas for 1 h. The reaction mixture was stirred at room temperature overnight followed by solvent removal in vacuo. The residue was dried in vacuum desiccator to give 3.2 g of ester [FAB-MS: MH+ =238]. This material was used without any further purification.

Step 2 Preparation of ethyl β-[[4-[[4-(aminoiminomethyl)phenyl]amino]-1,4-dioxobutyl]amino]-1,3-benzodioxole-5-propanoate.

4-Succinylamidobenzamidine. HCl (2.75 g; 10 mmol; from Example 1, Step 1) was dissolved in DMF (50 ml). Isobutylchloroformate (1.5 g; 11 mmol) was added dropwise with stirring followed by N-methylmorpholine (1 g; 10 mmole). In a separate flask, ethyl β-amino-1,3-benzoxazole-5-propanoate. HCl (3 g, 12.5 mmoles) and N,N-diisopropyl-N-ethylamine (1.3 g; 10 mmol) were dissolved in DMF (20 ml). Both solutions were combined and stirred at room temperature for two h. Saturated sodium bicarbonate solution (30 ml) was added with stirring and the mixture was filtered. The filtrate was taken down to dryness on rotavapor. The remaining residue was purified by RPHPLC using a linear gradient of 10–40% acetonitrile/H2O/0.05% TFA in 30 min; MS FAB 454 (MH+). $^1$H NMR (DMSO-d6) δ1.11 (t, 3H, $CO_2CH_2CH_3$), 2.45 and 2.57 (t, 4H, $COCH_2CH_2CO$), 2.69 (d, 2H, $CH_2CO_2CH_2CH_3$), 4.0 (q, 2H, $CO_2CH_2CH_3$), 5.13 (q, 1H, NHCH), 5.97 (s, 2H, $OCH_2O$), 6.8 and 6.9 (b, 3H, Ar), 7.77 (s, 4H, Ar), 8.48 (d, 1H, CONH), 8.87 and 9.15 (s, 4H, $H_2NCNH_2$).

Elemental analysis:$C_{23}H_{23}N_4O_6$.$CF_3COOH$ Calculated: C 52.81 H 4.79 N 9.85 Found: C 52.10 H 4.75 N 9.75

EXAMPLE 20

β-[[4-[[4-(aminoiminomethyl)phenyl]amino]-1,4-dioxobutyl]amino]-1,3-benzodioxole-5-propanoic acid

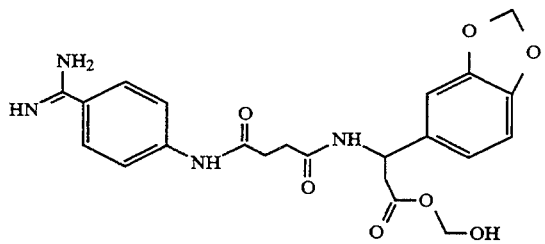

Ethyl β-[[4-[[4-aminoiminomethyl)phenyl]amino]-1,4-dioxobutyl]amino]-1,3-benzodioxole-5-propanoate (100 mg) was stirred in 2N LiOH (5 ml) and methanol (5 ml) at room temperature for 20 min. The mixture was neutralized with 4N HCl and diluted with water (20 ml). This material was then purified by RPHPLC using a gradient of 10–40% acetonitrile/H20/0.05% TFA in 30 min; MS(FAB) 426 (MH+). 'H-NMR (DMSO-d6) δ2.45 and 2.57 (t, 4H, COCH$_2$CH$_2$CO), 2.60 (d, 2H, CH$_2$CO$_2$H), 5.08 (q, 1H, NHCH), 5.97 (s, 2H, OCH$_2$O), 6.8 and 6.9 (b, 3H, Ar), 7.77 (s, 4H, Ar), 8.44 (d, 1H, CONH), 8.93 and 9.12 ( s, 4H, H$_2$NCNH$_2$).

Elemental analysis: C$_{21}$H$_{22}$N$_4$O$_6$·CF$_3$COOH Calculated: C 51.11 H 4.29 N 10.37 Found: C 50.30 H 4.16 N 10.19

EXAMPLE 21 ethyl β-[[4-4[[4(aminoiminomethyl)phenyl]amino]-1,4-dioxobutyl]amino]-2-nitro-1,3-benzodioxole-5-propanoate

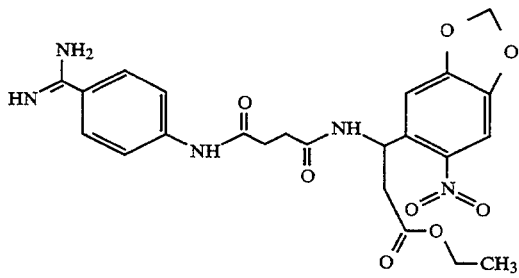

The ester was prepared and purified according to the procedure described in Example 20, Step 2, using ethyl β-amino-2-nitro-1,3-benzoxazole-5-propanoate; MS (FAB) 499.5 (MH+). $^1$H-NMR (DMSO-d6) δ1.16 (t, 3H, CO$_2$CH$_2$CH$_3$), 2.43 and 2.54 (t, 4H, COCH$_2$CH$_2$CO), 2.73 (d, 2H, CH$_2$CO$_2$CH$_2$CH$_3$), 4.06 (m, 2H, CO$_2$CH$_2$CH$_3$), 5.63 (m, 1H, NHCH), 6.20 (d, 2H, OCH$_2$O), 7.2 and 7.5 (s, 2H, Ar), 7.74 (s, 4H, Ar), 8.62 (d, 1H, CONH), 8.74 and 9.12 (s, 4H, H$_2$NCNH$_2$).

Elemental analysis: C$_{23}$H$_{25}$N$_5$O$_8$·CF$_3$COOH Calculated: C 48.94 H 4.27 N 11.42 Found: C 48.17 H 4.22 N 10.88

EXAMPLE 22

β-[[4-[[4-(aminoiminomethyl)phenyl]-amino]-1,4-dioxobutyl]-5-pyrimidinepropanoic acid

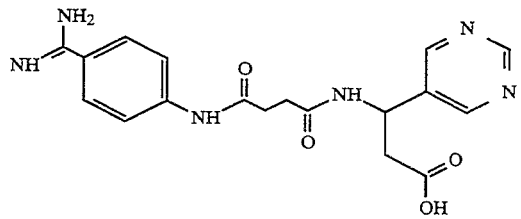

Step 1 Preparation of t-butyl (5-pyrimidinyl)acrylate.

A mixture of 30 g 5-bromopyrimidine, 1.2 g palladium acetate, 25 mL triethylamine and 250 ml t-butyl acrylate was heated at 80° C. for 5 days. The resulting mixture was concentrated to a waxy solid in vacuo. The residue was taken up in ethyl acetate and filtered. The filtrate was kept in the cold (−20° C., hexane added), and 10.5 g of tan needles deposited: $^1$H NMR (300 MHz) (d6-DMSO) δ1.45 (s, 9H), 6.1 (d, 1H, J=12.3 Hz), 6.8 (d, H, J=12.3 Hz), 8.85 (s, 1H), 9.15 (s, 1H); MS (FAB) m/e (MH+): 206.2

Elemental analysis: C$_{11}$H$_{14}$N$_2$O$_2$ Calculated: C 64.06 H 6.84 N 13.58 Found: C 63.83 H 6.95 N 13.20

Step 2 Preparation of t-butyl-3-amino-3-(5-pyrimidinyl) propanoate, trifluoroacetate.

Methanol saturated with ammonia (100 ml) was added to t-butyl (4-pyrimidinyl)acrylate (4 g) and allowed to stir at 80° C. for 5 days. The excess ammonia in methanol was removed under reduced pressure and the desired amino ester separated by HPLC. The appropriate fractions (R$_t$=13 min on a gradient of 10–40% acetonitrile/H$_2$O/0.05% TFA in 30 min; R$_f$ SiO$_2$ MeOH:CHC$_{13}$ 1:9 0.36) were lyophilized to give 1 g of white powder: $^1$H NMR (300 MHz) (d6-DMSO) δ1.25 (s, 9H), 2.95 (m, 1H), 2.15 (m, 1H), 8.85 (s, 1H), 9.15 (s, 1H); MS (FAB) m/e 23.2 (MH+).

Step 3 Preparation of β-[[4-[[4-aminoiminomethyl)-phenyl]-amino]-1,4-dioxobutyl]-5-pyrimidinepropanoic acid.

4-[[4-(Aminoiminomethyl)phenyl]-amino]-4-oxobutanoic acid hydrochloride prepared in Example 1, Step 1 (270 mg, 1 mmol) was added to dry DMF (50 ml) followed by N-methylmorpholine (110 uL, 1 mmol) and isobutyl chloroformate (140 uL, 1.1 mmol) at 25° C. The mixture was stirred for 5 min, and then a mixture of t-butyl-3-amino-3-(5-pyrimidinyl) propanoate trifluoroacetate (300 mg, 0.9 mmol) in 10 mL DMF and 140 uL NMM was added. After 1 h, the solvent was removed under reduced pressure and the product purified by RPHPLC (water/acetonitrile) to result in 6.0 g of a white solid. This material was stirred in 50 mL of a 1:1 mixture of dichloromethane and trifluoroacetic acid for 16 h at room temperature. The acid was purified by RPHPLC (water/acetonitrile) to result in 200 mg of a white solid: mp 187–92; $^1$H NMR (d6-DMSO) δ2.45 (m, 2H), 2.6 (m, 2H), 2.75 (d, 2H, J=7.6 Hz), 5.15 (dd, J and J=7.5 Hz, 1H), 7.75 (s, 4H), 8.6 (d, 1H, J=7.5 Hz), 8.75 (s, 2H), 8.9 (bs, 2H), 9.05 (s, 1H), 9.19 (bs, 2H), 10.42 (s, 1H); MS (FAB)m/e 385.2 (MH+).

Elemental analysis: C$_{18}$H$_{20}$N$_6$O$_4$. 1.5 TFA Calculated: C 45.06 H 4.18 N 15.01 Found: C 45.00 H 3.86 N 15.02

EXAMPLE 23

Preparation of ethyl 3-[[4-[[4-(aminoiminomethyl)phenyl]-amino]-1,4-dioxobutyl]-5-pyrimidinepropanoate

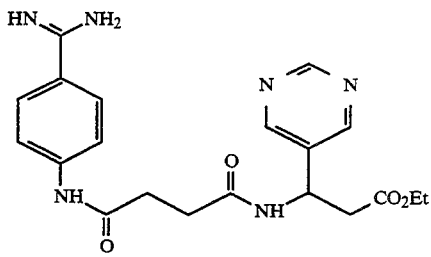

Step 1 Ethyl 3-amino-3-(5-pyrimidinyl)propanoate, hydrochloride.

The t-butyl 3-amino-3-(5-pyrimidinyl)propanoate trifluoroacetate salt (1 g), prepared as in example 22, Step 2 was dissolved in 100 mL dry ethanol and 10 mL 4N HCl in dioxane and stirred at room temperature until transesterification was complete. The solvents were removed in vacuo and the residue taken up in ethyl acetate and diethyl ether. The resulting precipitate was filtered, washed with ether and dried (0.8 g) $^1$H NMR (300 MHz) (d6-DMSO) d 1.05 (t, J=7 Hz, 3H), 3.25 (m, 2H), 4.05 (q, J=7 Hz, 2H), 4.7 (m, 1H), 9.05 (s, 1H), 9.25 (s, 1H)

Step 2 Preparation of ethyl 3-[[4-[[4-(aminoiminomethyl)phenyl]-amino]-1,4-dioxobutyl]-5-pyrimidinepropanoate.

Ethyl 3-amino-3-(5-pyrimidinyl)propanoate prepared in Example 23, Step 1(975 mg, 3.6 mmol) was added to dry DMF (60 ml) followed by N-methylmorpholine (400 uL, 3.5 mmol) and isobutyl chloroformate (500 uL, 3.8 mmol) at 25° C. The mixture was stirred for 5 min, and then a mixture of ethyl-3-amino-3-(5-pyrimidinyl)propanoate, hydrochloride. (850 mg, 3.5 mmol) in 10 mL DMF and 500 uL NMM was added. After 16 h, the solvent was removed under reduced pressure and the product purified by RPHPLC (water/acetonitrile) to result in 0.9 g of a white solid mp 168°–9° C. $^1$H NMR (d6-DMSO) δ1.1 (t, J=7 Hz, 3H) 2.46 (m, 2H), 2.6 (m, 2H), 2.9 (m, 2H), 4.05.(q, J=7 Hz, 2H) 5.2 (m, 1H); 7.75 (s, 4H), 8.6 (d, 1H, J=8 Hz), 8.75 (s, 2H), 8.9 (bs, 2H), 9.05 (s, 1H), 9.14 (bs, 2H), 10.37 (s, 1H); MS (FAB) m/e 413.4 (MH+).

Elemental Analysis $C_{20}H_{24}N_6O_4 \cdot TFA_1H_2O$ Calculated: C 48.60 H 4.99 N 15.46 Found: C 48.59 H 4.77 N 15.36

EXAMPLE 24

β(S)-[[[2-[[[4-(aminoiminomethyl)phenyl]amino]carbonyl]cyclopropyl]carbonyl]amino]-3-pyridinepropanoic acid, bis(trifluoroacetate), isomer 1

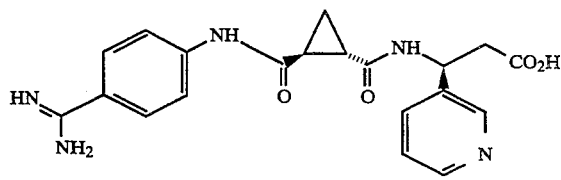

Step 1 Preparation of [2-[ethoxycarbonyl]cyclopropyl]-carboxylic acid.

Diethyl cyclopropyldicarboxylate (50 g, 0.268 mol; trans isomer from Aldrich) in 100 mL ethanol was added to a solution of 10 g LiOH (0.238 mol) in 100 mL H2O. After 5 min stirring, a yellow homogeneous mixture was observed and stirring continued for 24 h at 25° C. The crude reaction mixture was partitioned between ethyl acetate and water (pH=9). Then the aqueous layer was made acidic (pH 2), and extracted with ethyl acetate. The ethyl acetate extract was dried (MgSO4), and concentrated to give 27 g of the desired mono acid as a solid: mp 46° C.

Step 2 Preparation of ethyl [2-[[[4-(aminoiminomethyl)-phenyl]amino]carbonyl]cyclopropyl]carboxylate.

[2-[ethoxycarbonyl]cyclopropyl]carboxylic acid (1.6 g) in 20 mL dichloromethane was stirred with 3×2 mL oxalyl chloride in the space of 16 h at 25° C. The solvents were removed in vacuo and the residue was dissolved in 50 mL pyridine and 10 mL DMF. A solution of 1.55 g aminobenzamidine dihydrochloride in 25 mL pyridine, 25 mL DMF and 3 mL NMM was added and the mixture stirred at 25° C. for 48 h. The reaction mixture was concentrated, water added (50 mL) and the pH adjusted to 10.5. A creamy precipitate was filtered and dried (300 mg); MS (FAB) m/e 248.2 (MH+).

The product was dissolved in 25 mL 2N hydrochloric acid and stirred at 25° C. for 16 hr. The reaction mixture was concentrated in vacuo and the remaining slurry lyophilized from 25 mL water to afford a tan solid. The ethyl acetate extract contained 15 g of a mixture 2:1 of monoethyl ester: diacid. A portion of this mixture (7.5 g) was suspended in dichloromethane and treated with a total of 67 mL oxalyl chloride at room temperature for a total time of 20 h. After concentration in vacuo, the residual oil was taken up in 20 mL dimethylformamide and a mixture of aminobenazamidine dihydrochloride (12.5 g, 0.06 mol) and 15 mL of triethyl amine in 50 mL dimethylformamide was slowly added. After 16 h stirring at 25°, the reaction was concentrated and the residue taken up in H2O/acetonitrile and purified by RPHPLC. The major peak (detection at 225 nM) was collected ($R_t$ on a linear H2O:ACN 5:95–70:30 over 25 min is 16 min). Lyophilization gave 730 mg of a white powder; MS(FAB) m/e 276.2 (MH+).

Step 3 Preparation of 2-[[[4-(aminoiminomethyl)phenyl]amino]carbonyl]cyclopropyl-carboxylic acid.

The product prepared above was stirred in a solution of 1 g LiOH, 5 mL acetonitrile and 10 mL H2O for 6 h at room temperature. A precipitate appeared upon adjusting the pH to 6 and upon concentration. The precipitate was collected, redissolved in H2O: acetonitrile and pH brought to 2 with HCl. This solution after lyophilization gave 480 mg of tan solid: $^1$H NMR (CD3OD) δ1.3 (m, 2H), 1.95 (m, 1H), 2.12 (m, 1H), 7.6 (m, 4H).

Step 4 Preparation of ethyl [[[2-[[[4-(aminoiminomethyl)phenyl]amino]carbonyl]cyclopropyl]carbonyl]amino]-3-pyridinepropanoate, bis(trifluoroacetate).

The acid prepared in step 2 (210 mg; 0.7 mmol) was coupled to 420 mg of ethyl β-(S)-amino-3-pyridinepropanoate ditrifluoroacetate using the mixed anhydride procedure similar to that described in Example 7. After concentration in vacuo, the residue (800 mg brownish oil) was purified by RPHPLC (H2O:ACN:0.05%TFA). Two products, one eluting at 12 min and the second at 13.2 min ($R_t$ on a linear H2O:ACN 5:95–70:30 over 25 min), were collected which after lyophilization provided respectively 120 mg and 100 mg of white solids.

Step 5 Preparation of β(S)-[[[2-[[[4-(aminoiminomethyl)phenyl]amino] carbonyl]cyclopropyl]carbonyl]amino]-3-pyridinepropanoic acid, bis(trifluoroacetate).

The ester (isomer 1, $R_t$ 12 min, 120 mg) isolated above was dissolved in 10 mL $H_2O$ and LiOH was added to pH 12. The reaction was stirred for 2 h at 25° C. After acidification to pH 4 with TFA, the reaction mixture was purified by RPHPLC. The main peak ($R_t$ 10.3 min) was collected and lyophilized to 64 mg of white powder: MS (FAB) m/e 396.4(MH+); $^1$H NMR 500 MHz (DMSO) δ1.16 (m, 2H), 1.25 (m, 2H), 2.16 (m, 1H), 2.26 (m, 1H), 2.80 (m, 2H), 5.20 (m, 1H), 7.5 (m, 1H), 7.75 (m, 4H), 7.95 (m, 1H), 8.5 (m, 1H), 8.6 (s, 1H), 8.9 (bs, 2H), 8.96 (d, 1H, J=8 Hz), 9.2 (bs, 2H), 10.8 (s, 1H); [α]D= −89.2° (C 0.06, $H_2O$, pH=3).

EXAMPLE 25

(S)-[[[2-[[[4-(aminoiminomethyl)phenyl]amino]carbonyl]cyclopropyl]carbonyl]amino]-3-pyridinepropanoic acid, bis(trifluoroacetate) isomer 2.

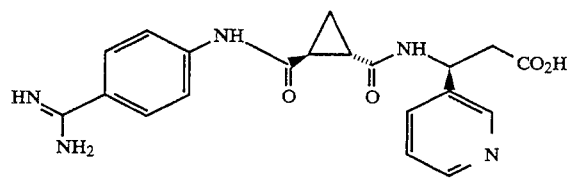

The second ester (isomer 2, Rt 13.2 min, 100 mg) isolated in Step 3 of Example 24 was dissolved in 10 mL $H_2O$ and LiOH was added to pH 12. The reaction was stirred for 2 h at 25° C. After acidification to pH 4 with TFA, the reaction mixture was purified by RPHPLC. The main peak ($R_t$ 10.4 min) was collected and lyophilized to 64 mg of white powder: MS (FAB) m/e 396.4(MH+); $^1$H NMR 500 MHz (DMSO) δ1.16 (m, 2H ), 1.25 (m, 2H), 2.16 (m, 2H), 2.80 (m, 2H), 5.20 (m, 1H), 7.5 (m, 1H), 7.75 (m, 4H), 7.95 (m, 1H), 8.55 (m, 1H), 8.6 (s, 1H), 8.9 (bs, 2H), 8.96 (d, 1H, J=8 Hz), 9.12 (bs, 2H), 10.78 (s, 1H);[a]D +112.5° (C 0.05, $H_2O$, pH=3).

EXAMPLE 26

β(R)-[[[2-[[[4-(aminoiminomethyl)phenyl]amino]carbonyl]cyclopropyl]carbonyl]amino]-3 -pyridinepropanoic acid, bis(trifluoroacetate), isomer 1.

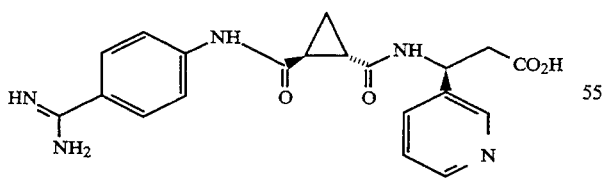

Step 1 Preparation of ethyl β- (R)-[[[2-[[[4-(aminoiminomethyl)phenyl]amino]carbonyl]cyclopropyl]carbonyl]amino]-3-pyridinepropanoate, his(trifluoroacetate).

The acid prepared in Example 24 Step 2 (283 mg; 1.1 mmol) was coupled to 420 mg of ethyl β-(S)-amino-3-pyridinepropanoate ditrifluoroacetate using the mixed anhydride procedure similar to that described in Example 7. After concentration in vacuo, the residue (800 mg brownish oil) was purified by RPHPLC ($H_2O$:ACN:0.05%TFA). Two products, one eluting at 12 min and the second at 13.2 min ($R_t$ on a linear $H_2O$:ACN 5:95–70:30 over 25 min), were collected which after lyophilization provided respectively 300 mg and 100 mg of white solids.

Step 2 Preparation of β(R)-[[[2-[[[4-(aminoiminomethyl)phenyl]amino] carbonyl]cyclopropyl]carbonyl]amino]-3-pyridinepropanoic acid, bis(trifluoroacetate).

The ester (isomer 1, $R_t$ 12 min, 120 mg) isolated above was dissolved in 10 mL $H_2O$ and LiOH was added to pH 12. The reaction was stirred for 2 h at 25° C. After acidification to pH 4 with TFA, the reaction mixture was purified by RPHPLC. The main peak ($R_t$ 10.3 min) was collected and lyophilized to 40 mg of white powder: MS (FAB) m/e 396.4(MH+); $^1$H NMR 500 MHz (DMSO) δ1.16 (m, 2H), 1.25 (m, 2H), 2.16 (m, 1H), 2.26 (m, 1H), 2.80 (m, 2H), 5.20 (m, 1H), 7.5 (m, 1H), 7.75 (m, 4H), 7.95 (m, 1H), 8.5 (m, 1H), 8.6 (s, 1H), 8.9 (bs, 2H), 8.96 (d, 1H, J=8 Hz), 9.2 (bs, 2H), 10.8 (s, 1H).

Elemental analysis: $C_{24}H_{25}N_5O_9F_6$ Calculated: C 44.9 H 3.9 N 10.9 Found: C 44.66 H 3.59 N 10.77

Example 27

β(R)-[[[2-[[[4-(aminoiminomethyl)phenyl]amino]carbonyl]cyclopropyl]carbonyl]amino]-3-pyridinepropanoic acid, bis(trifluoroacetate), isomer 2.

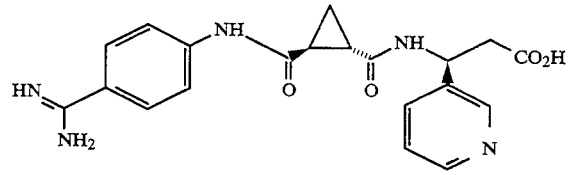

The second ester (isomer 2, $R_t$ 13.2 min, 100 mg) isolated in Step 1 of Example 26 was dissolved in 10 mL $H_2O$ and LiOH was added to pH 12. The reaction was stirred for 2 h at 25° C. After acidification to pH 4 with TFA, the reaction mixture was purified by RPHPLC. The main peak ($R_t$ 10.4 min) was collected and lyophilized to 55 mg of white powder: MS (FAB) m/e 396.4(MH+); $^1$H NMR 500 MHz (DMSO) δ1.16 (m, 2H), 1.25 (m, 2H), 2.16 (m, 2H), 2.80 (m, 2H), 5.20 (m, 1H), 7.5 (m, 1H), 7.75 (m, 4H), 7.95 (m, 1H), 8.55 (m, 1H), 8.6 (s, 1H), 8.9 (bs, 2H), 8.96 (d, 1H, J=8 Hz), 9.12 (bs, 2H), 10.78 (s, 1H);[α]D −112.2° (C 0.06, $H_2O$, pH=3).

Elemental Analysis: $C_{11}H_{14}N_2O_2$ calculated: C 44.9 H 3.9 N 10.9 Found: C 44.26 H 3.53 N 10.72

Example 28

Methyl [[4-[[4-(aminoiminomethyl)phenyl]amino]-1,4-dioxobutyl]amino]-3-pyridinepropanoate

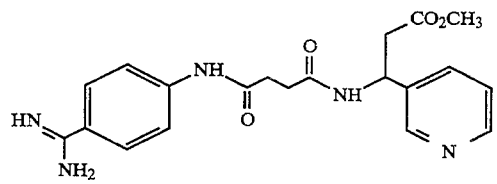

Step 1 4-[[4-(aminoiminomethyl)phenyl]-amino]-4-oxobutanoic acid hydrochloride prepared in Example 1, Step 1 (5.0 g, 18.5 mmol) was added to dry DMF (250 ml) followed by N-methylmorpholine (1.7 g, 18.5 mmol) and isobutyl chloroformate (2.8 g, 17 mmol) at 25° C. The mixture was stirred for 5 min. Methyl 3-amino-3-pyridinepropanoate (3.0 g, 18.5 mmol) was added followed by dimethylaminopyridine. After 1 h, the solvent was removed under reduced pressure and the product purified by RPHPLC (water/acetonitrile) to result in 2.0 g of a white solid: $^1$H NMR (d$_6$-DMSO) δ2.57 (t, 2H, J=7.31 Hz), 2.07 (t, 2H, J=7.1 Hz), 3.47 (t, 2H, J=7.0 Hz), 3.5 (s, 6H), 3.51 (m, 1H), 7.79 (s, 4H), 8.1 (t, 1H, J=7.1 Hz), 8.7 (bs, 2H), 9.09 (bs, 2H), 10.32 (s, 1H); MS (FAB) m/e 379.0 (MH+).

Elemental Analysis Required for $C_{17}H_{22}N_4O_6$ . $F_3C_2O_2H$ . $H_2O$ C 4 5.50 H 4.72 N 11.18 Found: C 4 5.20 H 4.66 N 11.17

EXAMPLE 29

(±)
[[[4-[[4-(aminoiminomethyl)phenyl]-amino]-1,4-dioxo-(2E)-butenyl]amino]-3-pyridinepropanoic acid

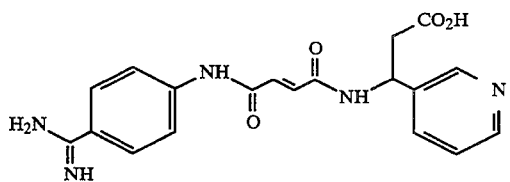

Step 1 Preparation of 4-[[4-(aminoiminomethyl)phenyl]amino]-4-oxo-buten-(E)-oic acid.

In a round bottomed flask under a static atmosphere of dry nitrogen were mixed 1.4 g of monoethyl fumarate, 1.36 g of isobutyl chloroformate and 1.01 g N-methylmorpholine in 100 mL DMF. 4-aminobenzamidine dihydrochloride (2.06 g) and 2.02 g N-methylmorpholine were added at room temperature and the reaction mixture was stirred at 25° C. for 30 min. Water and sodium hydroxide were added to pH 10 and after one hour stirring neutralized to pH 7 to precipitate the zwitterion. Filtration provided 1 g of the desired compound as a white solid: $^1$H NMR (d$_6$-DMSO) δ1.1 (t, 3H, J=7 Hz), 2.45 (m, 2H), 2.6 (m, 2H), 2.75 (d, 2H, J=7 Hz), 4.0 (q, 2H, J=7 Hz), 4.2 (dd, 1H, J=7 Hz and 8 Hz), 7.3 (m, 4H), 7.8 (s, 4H), 8.45 (d, 1H, J=8 Hz), 9.05 (bs, 2H), 9.2 (bs, 2H), 10.4 (s, 1H).

Step 2 4-[[4-(aminoiminomethyl)phenyl]-amino]-4-oxobuten-(E)-oic acid hydrochloride prepared in Step 1 (5.0 g, 18.5 mmol) was added to dry DMF (250 ml) followed by N-methylmorpholine (1.7 g, 18.5 mmol) and isobutyl chloroformate (2.8 g, 17 mmol) at 25° C. The mixture was stirred for 5 min. Ethyl-3-amino-3-(pyridyl)-propanoate (3.0 g, 18.5 mmol) was added followed by dimethylaminopyridine. After 1 h, the solvent was removed, and LiOH in 25 ml water was added to hydrolyze to the acid. After complete reaction, the solution was made acidic and the product purified by RPHPLC (water/acetonitrile 0.05% TFA) to result in 2.0 g of a white solid: $^1$H NMR (d$_6$-DMSO) δ2.57 (t, 2H, J=7.3 Hz), 2.07 (t, 2H, J=7.1 Hz), 3.47 (t, 2H, J=7.0 Hz), 3.5 (s, 6H), 3.51 (m, 1H), 7.79 (s, 4H), 8.1 (t, 1H, J=7.1 Hz), 8.7 (bs, 2H), 9.09 (bs, 2H), 10.32 (s, 1H); MS (FAB) m/e 379.0 (MH+).

Elemental Analysis Required for $C_{17}H_{22}N_6$ . $F_3C_2O_2H$ . $H_2O$: C 45.50 H 4.72 N 11.18 Found: C 45.20 H 4.66 N 11.17

EXAMPLE 30

(±)-1
[[[4-[[4-(aminoiminomethyl)phenyl]amino]-1,4-dioxo-(2 Z)-butenyl]amino]-3-pyridinepropanoic acid

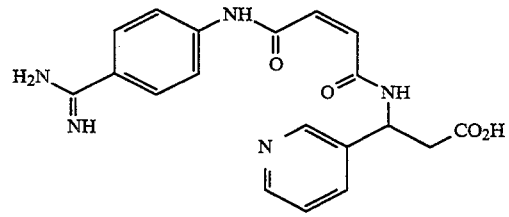

Step 1 4-[[4-(aminoiminomethyl)phenyl]-amino]-4-oxobut-(z)-oic acid hydrochloride prepared from maleic anhydride and aminobenzamidine in the manner of Example 1, Step 1 (5.0 g, 18.5 mmol) was added to dry DMF (250 ml) followed by N-methylmorpholine (1.7 g, 18.5 mmol) and isobutyl chloroformate (2.8 g, 17 mmol) at 25° C. The mixture was stirred for 5 min. Ethyl-3-amino-3-(pyridyl)-propanoate (3.0 g, 18.5 mmol) was added followed by dimethylaminopyridine. After 1 h, the solvent was removed, and LiOH in 25 ml water was added to hydrolyze to the acid. After complete reaction the solution was made acidic and the product purified by RPHPLC (water/acetonitrile 0.05% TFA) to result in 2.0 g of a white solid: $^1$H NMR (d$_6$-DMSO) δ2.57 (t, 2H, J=7.3 Hz), 2.07 (t, 2H, J=7.1 Hz), 3.47 (t, 2H, J=7.0 Hz), 3.5 (s, 6H), 3.51 (m, 1H), 7.79 (s, 4H), 8.1 (t, 1H, J=7.1 Hz), 8.7 (bs, 2H), 9.09 (bs, 2H), 10.32 (s, 1H); MS (FAB) m/e 379.0 (MH+).

Elemental Analysis Required for $C_{17}H_{22}N_4O_6$ . $F_3C_2O_2H$ . $H_2O$: C 45.50 H 4.72 N 11.18 Found: C 45.20 H 4.66 N 11.17

EXAMPLE 31

Ethyl β-[[4-[[4-(aminoiminomethyl)phenyl]amino]1,4-dioxobutyl]amino]-1,3-benzodioxole-5-propanoate (isomer 1)

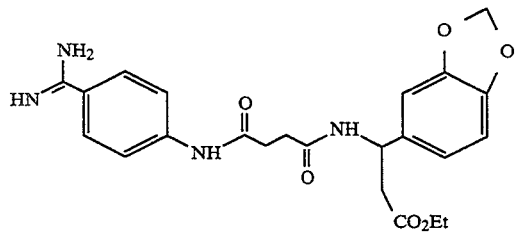

Step 1 Preparation of β-amino-[1,3-benzodioxole-5]propanoic acid 3,4-methylenedioxybenzaldehyde (12.0 g; 80 mmol), malonic acid (10.5 g; 50 mmol) and ammonium acetate (8 g; 104 mmol) were gently refluxed in ethanol (600 ml) overnight. The reaction mixture was hot filtered and the solid was washed with ethanol/water (1:1:3×100 ml). The product was air dried to yield 8 g of white material; MS(FAB) m/e 210 (MH+).

Step 2 Preparation of β-[[N-t-butoxycarbonylamido]-1,3-benzodioxole-5]propanoic acid β-amino-[1,3-benzodioxole-5]propanoic acid (2.1 g; 10 mmol) was dissolved in 2.5N NaOH (5 ml) and dioxane/water (2:1; 30 ml). To this mixture, Di-t-butyl-dicarbonate (2.62 g; 12 mmol) was added with vigorous stirring. The reaction mixture was allowed to stir at room temperature overnight and taken down to dryness on rotavapor. The residue was redissolved in water (100 ml), and the solution was acidified with a dilute solution of $KHSO_4$. The white precipitate was then collected by filtration, and dried in vacuo to yield 1.35 g of white solid; MS(FAB) m/e 332 (M+Na).

Step 3 Preparation of 2-[[β-N-t-butyloxycarbonylamido-1,3-benzodioxole-5]-propanoylamido]-2-phenylethanol β-[[N-t-butyloxycarbonylamido]-1,3-benzodioxole-5]propanoic acid (1.34 g; 4.34 mmol), disuccinimidyl-carbonate (1.5 g; 6 mmol) and 4-dimethylaminopyridine (300 mg) were stirred in DMF/pyridine (2:1; 50 ml) at ambient temperature overnight. To this solution, (R)-2-amino-2-phenylethanol (1.15 g; 8 mmol) was added and the stirring was allowed to continue for another day. The mixture was taken down to dryness on rotavapor and the residue was triturated with water. The solid was filtered and applied to RPHPLC. The diastereomeric mixture was separated using an isocratic condition of 35% acetonitrile/water. Both early and later peaks were collected and lyophilized. Both compounds have the same mass ion of M+Li=435.

step 4 Preparation of Ethyl β-amino-[1,3-benzodioxole-5]propanoate (later peak)

2-[[β-N-t-butyloxycarbonylamido-1,3-benzodioxole-5]-propanoylamido]-2-phenylethanol (0.42 g; 1 mmole) was suspended in conc. $H_2SO_4$ (2 ml) and dioxane/$H_2O$ (1:1; 20 ml). The mixture was refluxed for 16 h and taken down to dryness on rotavapor. The residue was redissolved in $H_2O$ (50 ml) and the mixture was titrated to pH 10 with 2.5N NaOH and extracted with chloroform (3×75 ml). The aqueous phase was neutralized with 3N HCl and taken down to dryness on rotavapor. The solid was treated with ether and filtered to give 170 mg solid [FAB-MS: MH+=210]. This material was suspended in absolute ethanol (100 ml) and the suspension was cooled in an ice bath and bubbled with HCl gas for 2 hrs. The mixture was stirred at room temperature overnight and filtered. The filtrate was taken down to dryness on rotavapor and the residue [165 mg; FAB-MS: MH+=238] was used without any further purification.

step 5 Preparation of Ethyl β-amino-[1,3-benzodioxole-5]propanoate (early peak)

2-[[β-N-t-butyloxycarbonylamido-1,3-benzodioxole-5]-propanoylamido]-2-phenylethanol (0.62 g; 1.5 mmole) was suspended in conc. $H_2SO_4$ (2 ml) and dioxane/$H_2O$ (1:1; 20 ml). The mixture was refluxed for 16 hrs and worked up as described above. The acid [230 mg; FAB-MS: MH+=210] was converted to its ethyl ester [240 mg; FAB-MS: MH+=238].

Step 6 Preparation of Ethyl β-[[4-[[4-(aminoiminomethyl)phenyl]amino]-1,4-dioxobutyl]amino]-1,3-benzodioxole-5-propanoate 4-succinylamidobenzamidine. HCl (540 mg; 2 mmoles) was dissolved in DMF (10 ml). Isobutyl-chloroformate (275 mg; 2 mmol) was added dropwise with stirring followed by N-methylmorpholine (200 mg; 2 mmol). In a separate flask, ethyl β-amino-1,3-benzodioxole-5-propanoate. HCl (165 mg, 1 mmol, early peak) and N,N-diisopropyl-N-ethylamine (130 mg; 1 mmol) were dissolved in DMF (10 ml). Both solutions were combined and stirred at room temperature for two hours. Saturated sodium bicarbonate solution (5 ml) was added with stirring and the mixture was filtered. The filtrate was taken down to dryness on rotavapor. The remaining residue was purified by RPHPLC using a linear gradient of 10–40% acetonitrile/$H_2O$/0.05% TFA in 30 min; MS(FAB) 455 (MH+). $^1$H-NMR (DMSO-d$_6$) δ1.11 (t, 3H, $CO_2CH_2CH_3$), 2.45 and 2.57 (t, 4H, $COCH_2CH_2CO$), 2.69 (d, 2H, $CH_2CO_2CH_2CH_3$), 4.0 (q, 2H, $CO_2CH_2CH_3$), 5.13 (q, 1H, NHCH), 5.97 (s, 2H, $OCH_2O$), 6.8 and 6.9 (2s, 3H, Ar), 7.79 (s, 4H, Ar), 8.42 (d, 1H, CONH), 9.0 and 9.24 (2s, 4H, $H_2NCNH_2$).

Elemental analysis: $C_{23}H_{26}N_4O_6$.HCl.$H_2O$ Calculated: C 54.49 H 5.76 N 11.05 Found: C 54.39 H 5.49 N 11.01

EXAMPLE 32

β-[[4-4[[4-(aminoiminomethyl)phenyl]amino]-1,4-dioxobutyl]amino]-1,3 -benzodioxole-5-propanoic acid, isomer 2.

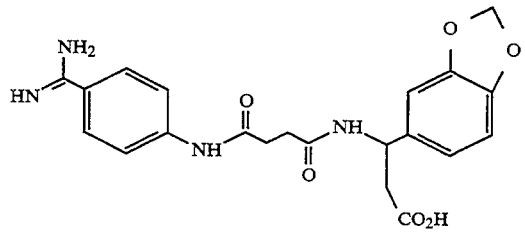

Ethyl β-[[4[[4-(aminoiminomethyl)phenyl]amino]-1,4-dioxobutyl]amino]-1,3-benzodioxole-5-propanoate (100 mg) was stirred in 2N LiOH (5 ml) and methanol (5 ml) at room temperature for 20 min. The mixture was neutralized with 4N HCl and diluted with water (20 ml). This material was then purified by RPHPLC using a gradient of 10–40% acetonitrile/$H_2O$/0.05% TFA in 30 min; MS(FAB) 427 (MH+). $^1$H-NMR (DMSO-d$_6$) δ2.45 and 2.57 (t, 4H, $COCH_2CH_2CO$), 2.60 (d, 2H, $CH_2CO_2H$), 5.08 (q, 1H, NHCH), 5.97 (s, 2H, $OCH_2O$), 6.8 and 6.9 (b, 3H, Ar), 7.77 (s, 4H, Ar), 8.4 (d, 1H, CONH), 8.97 and 9.15 (2s, 4H, $H_2NCNH_2$).

Elemental analysis: $C_{21}H_{22}N_4O_6$.HCl.$H_2O$ Calculated: C 52.45 H 5.24 N 11.65 Found: C 51.62 H 4.89 N 11.35

EXAMPLE 33

β[[4-[[4-(aminoiminomethyl)phenyl]amino]-1,4-dioxobutyl]amino]-1,3-benzodioxole-5-propanoic acid

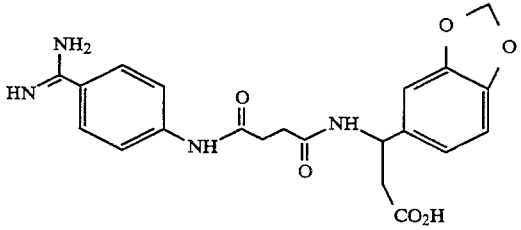

The ester was prepared and purified according to the procedure described in Example 31 Step 6 from the intermediate isolated in Example 31, Step 4 [FAB-MS: MH+=455; Example 32). This ester (50 mg) was treated with 2N LiOH (5 ml) and methanol (5 ml) at room temperature for 20 min. The mixture was neutralized with 4N HCl and diluted with water (20 ml). This material was then purified by RPHPLC using a gradient of 10–40% acetonitrile/$H_2O$/0.05% TFA in 30 min; MS(FAB) m/e (MH+) 427; $^1$H-NMR (DMSO-$d_6$) δ2.45 and 2.57 (t, 4H, $COCH_2CH_2CO$), 2.62 (d, 2H, $CH_2CO_2H$), 5.08 (q, 1H, $NH\overline{CH}$), 5.97 (s, 2H, $OCH_2O$), 6.78 and 6.9 (2s, 3H, Ar), 7.77 (s, 4H, Ar), 8.38 (d, 1H, CONH), 8.88 and 9.42 (2s, 4H, $H_2NCNH_2$).

Example 34

β-[[4-[[4-(aminoiminomethyl)phenyl]amino]-1,4-dioxobutyl]amino]-2-nitro-1,3-benzoxazole-5-propanoic acid

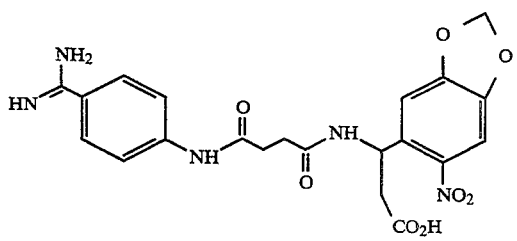

The acid was prepared and purified according to the procedure described in Example 20 using the ester prepared in Example 21. MS(FAB) 472.4 (MH+). $^1$H-NMR (DMSO-d6) δ2.45 and 2.54 (t, 4H, $COCH_2CH_2CO$), 2.65 (d, 2H, $CH_2CO_2CH_2CH_3$), 5.57 (m, 1H, NHCH), 6.20 (d, 2H, $OCH_2O$), 7.17 and 7.51 (2 s, 2H, Ar), 7.74 (s, 4H, Ar), 8.60 (d, 1H, CONH), 8.83 and 9.14 (2 s, 4H, $H_2NCNH_2$).

Elemental analysis: $C_{21}H_{21}N_5O_8 \cdot CF_3COOH \cdot H_2O$
Calculated: C 45.77 H 4.01 N 11.60 Found: C 45.96 H 3.69 N 11.36

In-Vitro Platelet Aggregation in PRP

Healthy male or female dogs were fasted for 8 hours prior to drawing blood; then 30 ml whole blood was collected using a butterfly needle and 30 cc plastic syringe with 3 ml of 0.129M buffered sodium citrate (3.8%). The syringe was rotated carefully as blood was drawn to mix the citrate. Platelet-rich plasma (PRP) was prepared by centrifugation at 975×x g for 3.17 minutes at room temperature allowing the centrifuge to coast to a stop without braking. The PRP was removed from the blood with a plastic pipette and placed in a plastic capped, 50 mL Corning conical sterile centrifuge tube which was held at room temperature. Platelet poor plasma (PPP) was prepared by centrifuging the remaining blood at 2000×x g for 15 minutes at room temperature allowing the centrifuge to coast to a stop without braking. The PRP was adjusted with PPP to a count of 2–3×$10^8$ platelets per mL. 400 uL of the PRP preparation and 50 uL of the compounds solution to be tested or saline were preincubated for 1 minute at 37° C. in a BioData, Horsham, PA). 50 uL of adenosine 5' diphosphate (ADP) (50 um final concentration) was added to the cuvettes and the aggregation was monitored for 1 minute. All compounds are tested in duplicate. Results are calculated as follows: Percent of control=[(maximal OD minus initial OD of compound) divided by (maximal OD minus initial OD of control saline)]×100. The % inhibition=100−(percent of control).

The compounds tested and their median inhibitory concentrations ($IC_{50}$) are recorded in Table I. $IC_{50}$'s (dosage at which 50% of platelet aggregation is inhibited) were calculated by linear regression of the dose response curve. The assay results for the compounds of Examples 1 to 22 are set forth in Table I below.

TABLE I

| Example | Dog PRP $IC_{50}$ | Ex Vivo Effect after IG Admins. |
|---|---|---|
| 1 | NT | + |
| 2 | 9.3 × $10^{-8}$ | NT |
| 3 | >10 | NT |
| 4 | NT | + |
| 5 | 4.7 × $10^{-8}$ | NT |
| 6 | NT | NT |
| 7 | 4.8 × $10^{-6}$ | NT |
| 8 | 2.9 × $10^{-7}$ | NT |
| 9 | NT | NT |
| 10 | 1.6 × $10^{-7}$ | NT |
| 11 | NT | NT |
| 12 | NT | NT |
| 13 | 2.9 × $10^{-7}$ | NT |
| 14 | 0 at $10^{-5}$ | NT |
| 15 | NT | + |
| 16 | NT | + |
| 17 | NT | + |
| 18 | 1.2 × $10^{-7}$ | NT |
| 19 | >10 | + |
| 20 | 6.8 × $10^{-8}$ | NT |
| 21 | >10 | −(5 mpk) |
| 22 | 5.9 × $10^{-8}$ | NT |
| 23 | NT | + |
| 24 | 6 × $10^{-8}$ | NT |
| 25 | 6 × $10^{-6}$ | NT |
| 26 | 8.0 × $10^{-7}$ | NT |
| 27 | >10 | NT |
| 28 | NT | + |
| 29 | 1.1 × $10^{-7}$ | NT |
| 30 | >10 | NT |
| 31 | 7.3 × $10^{-6}$ | + |
| 32 | 4 × $10^{-8}$ | NT |
| 33 | 6.8 × $10^{-6}$ | NT |
| 34 | 1.2 × $10^{-6}$ | NT |

NT - non tested

INHIBITION OF EX VIVO COLLAGEN INDUCED AGGREGATION BY COMPOUNDS OF THE INVENTION

Purpose

The purpose of this assay is to determine the effects of antiplatelet compounds on ex vivo collagen induced platelet aggregation when administered either intravenously or orally to dogs.

Pretreatment (control) blood samples are drawn from either conscious or anesthetized dogs (Beagles) and centrifuged to prepare platelet rich plasma (PRP). Aggregatory response to collagen is measured in a aggregometer and used as Control. Compounds are administered, either intragasterically (either by capsule or stomach tube or intravenously). Blood samples are drawn at predetermined intervals after compound administration, PRP prepared and aggregation to collagen determined. Compound inhibition of aggregation is determined by comparing the aggregation response after compound administration to the pretreatment response. The study is continued for a maximum of 24 hours or until the platelet aggregation returns to control levels. (If aggregation is still inhibited after 7 hours, a blood sample is drawn the following morning and tested.) Duration of activity is determined by the length of time platelet aggregation is inhibited after compound administration.

A representative compound of this invention, compound Examples #1, 4, and 16 were tested and inhibited up to 100% platelet aggregation after 24 hours when administered orally to dogs at a dose of 20 mg/kg.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound or a pharmaceutically acceptable salt, prodrug or ester thereof having the formula:

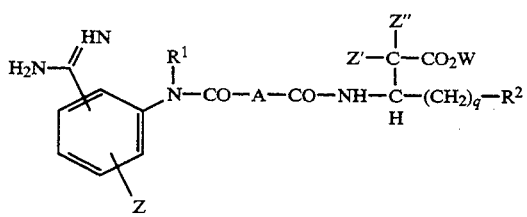

wherein $R^1$ is selected from the group consisting of hydrogen, lower alkyl radicals, lower alkenyl radicals, lower alkynyl radicals, alicyclic hydrocarbon radicals, aromatic hydrocarbon radicals, wherein all of said radicals are optionally substituted with hydroxyl, lower alkoxy, lower alkyl, halogen, nitro, carboxyl, sulfonyl, trifluoromethyl, amino, acyloxy, phenyl and naphthyl which are optionally substituted with halogen, nitro, lower alkoxy, and lower alkyl;

$R^2$ is selected from bicyclic heterocyclyl radicals in which 1 to about 3 heteroatoms are independently selected from oxygen, nitrogen and sulfur, which are optionally substituted with hydroxyl, lower alkoxy, lower alkyl, halogen, nitro, carboxyl, sulfonyl, trifluoromethyl, amino, acyloxy, phenyl and naphthyl which are optionally substituted with halogen, nitro, lower alkoxy, and lower alkyl;

A is selected from the group consisting of lower alkyl radicals, lower alkenyl radicals, lower alkynyl radicals, alicyclic radicals, wherein all of said radicals are optionally substituted with hydroxyl, lower alkoxy, lower alkyl, halogen, aromatic hydrocarbons which are optionally substituted with halogen, nitro, lower alkoxy and lower alkyl;

W is selected from the group consisting of hydrogen, lower alkyl radicals, lower alkenyl radicals, lower alkynyl radicals, alicyclic hydrocarbon radicals and aromatic hydrocarbon radicals, wherein all of said radicals are optionally substituted with hydroxyl, lower alkoxy, lower alkyl, halogen, nitro, amino, acyloxy, phenyl and naphthyl which may be optionally substituted with halogen, nitro, lower alkoxy, and lower alkyl;

Z, Z', Z" are independently selected from the group consisting of hydrogen, lower alkyl radicals, halogen, alkoxy, cyano, sulfonyl, carboxyl, and hydroxyl radicals; and q is an integer from 0 to about 6.

2. A compound as recited in claim 1 wherein $R^1$ is selected from the group consisting of hydrogen, lower alkyl radicals, lower alkenyl radicals, lower alkynyl radicals, alicyclic hydrocarbon radicals, aromatic hydrocarbon radicals; $R^2$ is selected from bicyclic heterocyclyl radicals in which 1 to about 3 heteroatoms are selected from oxygen, nitrogen and sulfur which are optionally substituted with hydroxyl, lower alkoxy, lower alkyl, halogen, nitro, carboxyl, sulfonyl, trifluoromethyl and amino;

A is selected from the group consisting of lower alkyl radicals, lower alkenyl radicals, lower alkynyl radicals, and alicyclic hydrocarbon radicals;

W is selected from the group consisting of hydrogen, lower alkyl radicals, lower alkenyl radicals, lower alkynyl radicals, alicyclic hydrocarbon radicals, and aromatic hydrocarbon radicals;

Z, Z', Z" are independently selected from the group consisting of hydrogen, lower alkyl radicals, halogen, alkoxy, cyano, sulfonyl, carboxyl, and hydroxyl radicals; and q is an integer from 0 to about 6.

3. A compound as recited in claim 1 wherein $R^1$ is selected from hydrogen, lower alkyl radicals of 1 to about 6 carbon atoms, lower alkenyl radicals of 2 to about 6 carbon atoms, lower alkynyl radicals of 2 to about 8 carbon atoms, alicyclic hydrocarbon radicals of 3 to about 6 carbon atoms, aromatic hydrocarbon radicals;

$R^2$ is selected from bicyclic heterocyclyl radical in which 1 to about 3 heteroatoms are selected from oxygen, nitrogen and sulfur which are optionally substituted with hydroxyl, lower alkoxy, lower alkyl, halogen, nitro, carboxyl, sulfonyl, trifluoromethyl and amino;

A is selected from lower alkyl radicals of 1 to about 6 carbon atoms, lower alkenyl radicals of 2 to about 6 carbon atoms, lower alkynyl radicals of 2 to about 4 carbon atoms, and, alicyclic hydrocarbon radicals of 3 to about 5 carbon atoms;

W is selected from hydrogen, lower alkyl radicals of 1 to about 6 carbon atoms, lower alkenyl radicals of 2 to about 6 carbon atoms, alicyclic hydrocarbon radicals of 3 to about 6 carbon atoms, and aromatic hydrocarbon radicals of 6 to about 12 carbon atoms;

Z, Z', Z" are independently selected from the group consisting of hydrogen, halogen, alkoxy, cyano, sulfonyl, carboxyl and lower alkyl radicals; and q is an integer from 0 to about 6.

4. A compound as recited in claim 1 wherein $R^1$ is selected from hydrogen, lower alkyl radicals, phenyl radicals, benzyl radicals, substituted phenyl radicals wherein each substituent is selected from the group consisting of halogen, lower alkyl, lower alkoxy and carboxyl radicals;

$R^2$ is a bicyclic heterocyclyl radical in which 1 to about 3 heteroatoms are nitrogen which heterocyclyl is optionally substituted with hydroxyl, lower alkoxy, lower alkyl, halogen, nitro, carboxyl, sulfonyl, trifluoromethyl and amino;

A is selected from lower alkyl radicals, lower alkenyl radicals and lower alicyclic hydrocarbon radicals;

W is selected from the group consisting of hydrogen and lower alkyl radicals;

Z, Z', Z" are independently selected from the group consisting of halogen, hydrogen, alkoxy, and lower alkyl radicals; and q is an integer from 0 to about 6.

5. A compound as recited in claim 1 wherein $R^1$ is selected from the group consisting of hydrogen, lower alkyl radicals, and benzyl radicals;

$R^2$ is benzodioxoyl which is optionally substituted with hydroxyl, lower alkoxy, lower alkyl, halogen, nitro, carboxyl, sulfonyl, trifluoromethyl and amino;

A is selected from the group consisting of lower alkyl radicals, lower alkenyl radicals and lower alicyclic hydrocarbon radicals;

W is selected from the group consisting of hydrogen and lower alkyl radicals;

z, Z', Z" are hydrogen; and q is an integer from 0 to about 4.

6. A compound as recited in claim 4 wherein "A" is selected from the group of methylene, ethylene, propylene, cyclopropylene or cyclohexylene.

7. A compound as recited in claim 1 which is ethyl β-[[4-[[4-(aminoiminomethyl)phenyl]amino]-1,4dioxobutyl]amino]-1,3-benzodioxole-5-propanoate.

8. A compound as recited in claim 1 which is ethyl βS-[[4-[[4-(aminoiminomethyl)phenyl]amino]-1,4-dioxobutyl]amino]-1,3-benzodioxole-5propanoate.

9. A compound as recited in claim 1 which is β-[[4-4[[4-(aminoiminomethyl)phenyl]amino]-1,4dioxobutyl]amino]-1,3-benzodioxole-5-propanoic acid.

10. A compound as recited in claim 1 which is βS-[[4-[[4-(aminoiminomethyl)phenyl]amino]-1,4-dioxobutyl]amino]-1,3-benzodioxole-5-propanoic acid.

11. A pharmaceutical composition comprising at least one non-toxic pharmaceutically acceptable carrier and at least one compound according to claim 1 together with said carrier.

12. A pharmaceutical composition comprising at least one non-toxic pharmaceutically acceptable carrier and at least one compound according to claim 2 together with said carrier.

13. A pharmaceutical composition comprising at least one non-toxic pharmaceutically acceptable carrier and at least one compound according to claim 3 together with said carrier.

14. A pharmaceutical composition comprising at least one non-toxic pharmaceutically acceptable carrier and at least one compound according to claim 4 together with said carrier.

15. A pharmaceutical composition comprising at least one non-toxic pharmaceutically acceptable carrier and at least one compound according to claim 5 together with said carrier.

16. A pharmaceutical composition comprising at least one non-toxic pharmaceutically acceptable carrier and at least one compound according to claim 7 together with said carrier.

17. A pharmaceutical composition comprising at least one non-toxic pharmaceutically acceptable carrier and at least one compound according to claim 8 together with said carrier.

18. A pharmaceutical composition comprising at least one non-toxic pharmaceutically acceptable carrier and at least one compound according to claim 9 together with said carrier.

19. A pharmaceutical composition comprising at least one non-toxic pharmaceutically acceptable carrier and at least one compound according to claim 10 together with said carrier.

20. A method of treating a mammal to inhibit platelet aggregation comprising administering a therapeutically effective amount of at least one compound of claim 1 to a mammal in need of such treatment.

21. A method of treating a mammal to inhibit platelet aggregation comprising administering a therapeutically effective amount of at least one compound of claim 2 to a mammal in need of such treatment.

22. A method of treating a mammal to inhibit platelet aggregation comprising administering a therapeutically effective amount of at least one compound of claim 3 to a mammal in need of such treatment.

23. A method of treating a mammal to inhibit platelet aggregation comprising administering a therapeutically effective amount of at least one compound of claim 4 to a mammal in need of such treatment.

24. A method of treating a mammal to inhibit platelet aggregation comprising administering a therapeutically effective amount of at least one compound of claim 5 to a mammal in need of such treatment.

25. A method of treating a mammal to inhibit platelet aggregation comprising administering a therapeutically effective amount of at least one compound of claims 7, 8, 9 or 10 to a mammal in need of such treatment.

* * * * *